United States Patent
Nakazono et al.

(10) Patent No.: US 8,016,965 B2
(45) Date of Patent: *Sep. 13, 2011

(54) INFORMATION STORING, READOUT AND CALCULATION SYSTEM FOR USE IN A SYSTEM FOR CONTINUOUSLY MANUFACTURING LIQUID-CRYSTAL DISPLAY ELEMENTS, AND METHOD FOR PRODUCING THE SAME

(75) Inventors: Takuya Nakazono, Osaka (JP); Seiji Umemoto, Osaka (JP); Fumihito Shimanoe, Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/903,937

(22) Filed: Oct. 13, 2010

(65) Prior Publication Data

US 2011/0083791 A1    Apr. 14, 2011

(30) Foreign Application Priority Data

Oct. 13, 2009   (JP) .................................. 2009-236091

(51) Int. Cl.
B32B 41/00    (2006.01)

(52) U.S. Cl. .......... 156/64; 156/252; 156/253; 156/360; 156/361; 156/378

(58) Field of Classification Search .................... 156/64, 156/252, 253, 269, 270, 271, 353, 360, 361
See application file for complete search history.

(56) References Cited

U.S. PATENT DOCUMENTS

| | | | |
|---|---|---|---|
| 2004/0095526 A1 | 5/2004 | Yamabuchi et al. | |
| 2004/0169809 A1 | 9/2004 | Yamabuchi et al. | |
| 2005/0199337 A1 | 9/2005 | Nishikubo et al. | |
| 2007/0013858 A1 | 1/2007 | Yamabuchi et al. | |
| 2009/0159175 A1 | 6/2009 | Nakahira et al. | |
| 2009/0199950 A1 | 8/2009 | Kitada et al. | |
| 2010/0288420 A1* | 11/2010 | Kimura et al. | 156/64 |

FOREIGN PATENT DOCUMENTS

| | | |
|---|---|---|
| EP | 2006715 | 12/2008 |
| EP | 2244244 | 10/2010 |
| JP | 57-052017 | 3/1982 |
| JP | 11-095028 | 4/1999 |

(Continued)

OTHER PUBLICATIONS

European Search Report for EP10186442.

(Continued)

*Primary Examiner* — George Koch
(74) *Attorney, Agent, or Firm* — Lowe Hauptman Ham & Berner LLP

(57) ABSTRACT

An information storage-readout-calculation system for use in a continuous manufacturing system of liquid-crystal display elements, comprising information storage medium for storing information of defects detected through a preliminary inspection of a continuous polarizing composite film included in a continuous optical film laminate, a roll of a continuous inspected optical film laminate being provided with identification means and a slitting position calculation means for determining defective-polarizing-sheet slitting positions to define defect-containing polarizing sheets having defects and normal-polarizing-sheet slitting positions to define defect-free polarizing sheets by using defect position information read out from the information storage medium based on the identification means, an, a method for manufacturing the information storage-readout-calculation system.

10 Claims, 22 Drawing Sheets

FOREIGN PATENT DOCUMENTS

| | | |
|---|---|---|
| JP | 2002-023151 | 1/2002 |
| JP | 2003-161935 | 6/2003 |
| JP | 2003-202298 | 7/2003 |
| JP | 2003-344302 | 12/2003 |
| JP | 2004-144913 | 5/2004 |
| JP | 2004-361741 | 12/2004 |
| JP | 2005-062165 | 3/2005 |
| JP | 2005-114624 | 4/2005 |
| JP | 2005-298208 | 10/2005 |
| JP | 2006-058411 | 3/2006 |
| JP | 2007-064989 | 3/2007 |
| JP | 2007-140046 | 6/2007 |
| JP | 2009-061498 | 3/2009 |
| TW | 200502649 | 1/2005 |
| TW | 200634358 | 10/2006 |
| WO | 2007/058023 | 5/2007 |
| WO | 2009/096388 | 8/2009 |
| WO | 2009/123002 | 10/2009 |
| WO | WO 2009128115 A1 * | 10/2009 |

OTHER PUBLICATIONS

Taiwanese office action dated Apr. 29, 2011 for application No. 099129094.

* cited by examiner

FIG.9

| inspection unit | types of defect | | | | |
|---|---|---|---|---|---|
| | internal foreign substances | internal pores | bright spots | surface irregularities | flaw/undulation |
| reflection | △ | △ | × | ○ | ○ |
| transmission | ○ | ○ | △ | △ | × |
| Cross-Nichol transmission | ○ | ○ | ○ | × | ○ |

FIG.11 types of identification indicia

| No | type | | type of information | data contents | effectiveness |
|---|---|---|---|---|---|
| 1 | one dimensional code<br>example: |  | alphameric characters | LOT No<br>No | ○ |
| 2 | two dimensional code<br>example: |  | alphameric characters<br>kana (Japanese syllabary)<br>kanji (Chinese character) | LOT No<br>No<br>distance | ○ |
| 3 | IC tag<br>example: |  | alphameric characters<br>kana (Japanese syllabary)<br>kanji (Chinese character) | LOT No<br>No<br>distance | ○ |
| 4 | label | | existence or nonexistence determination | starting point | △ |
| 5 | hole | | existence or nonexistence determination | starting point | △ |

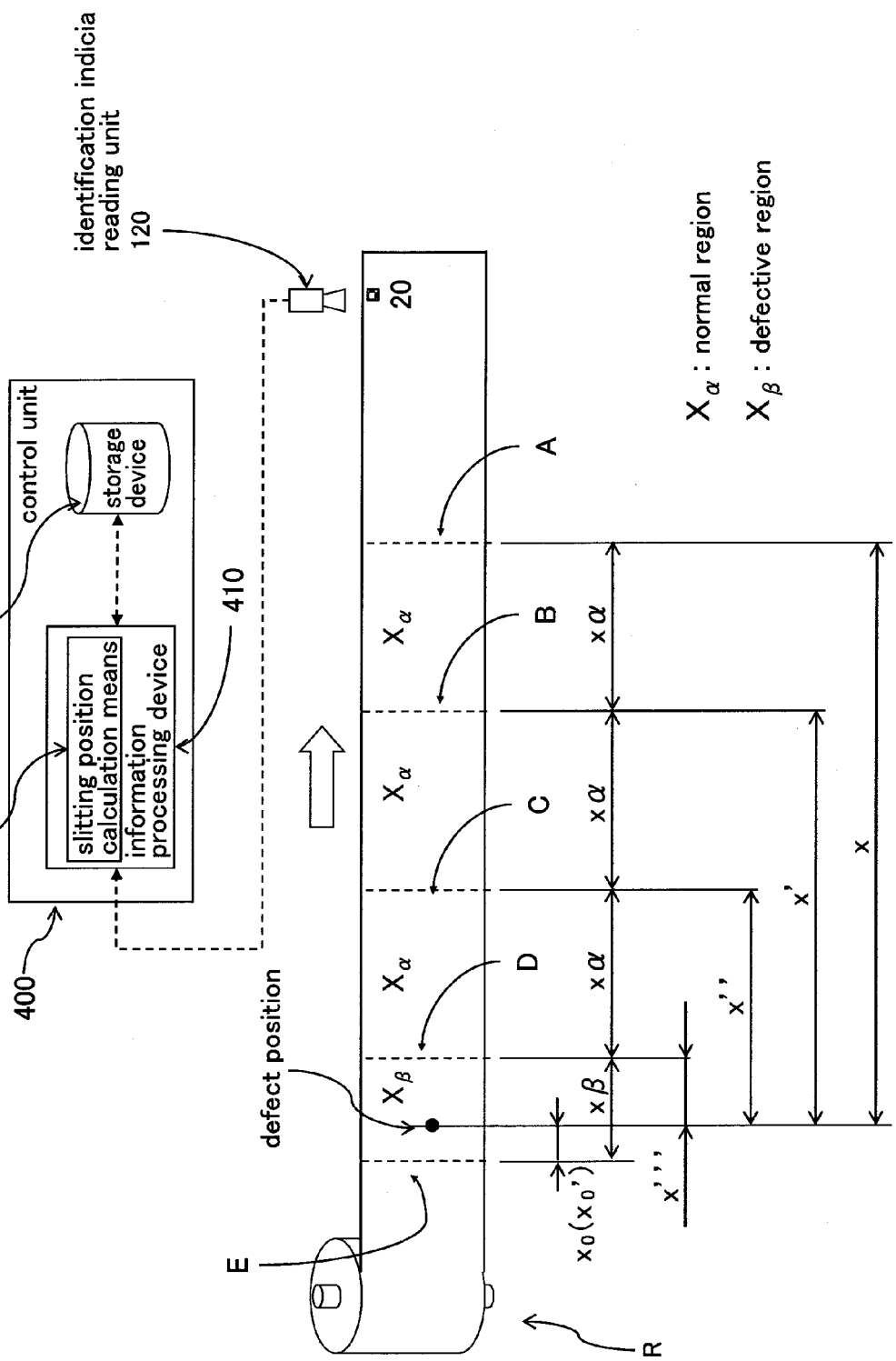

FIG.17 example of slitting position information

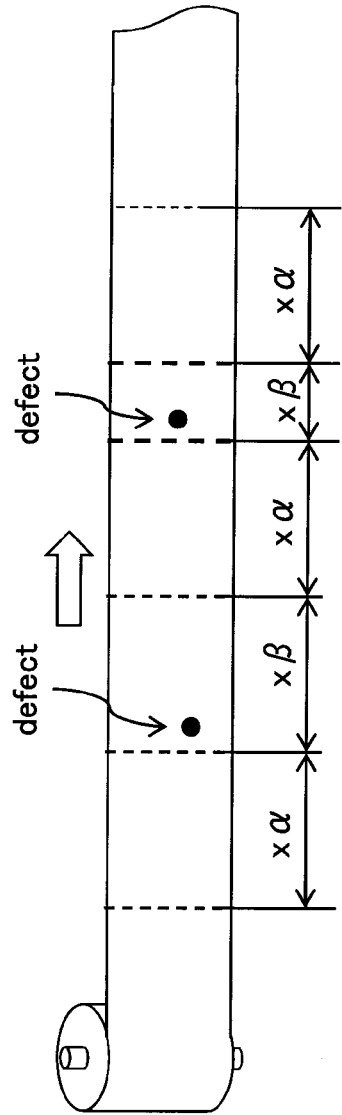

$x\alpha$ = size of product $x\beta$ = defective polarizing sheet ($x'+x_0$) ($x' \leq x\alpha$)

※ when $x\beta(x'+x_0) = x\alpha$,
$x\beta = x'+x_0'$ ($x_0 < x_0'$) $> x\alpha$ (in the table on left, $x_0' = x_0 + 5mm$)

| lot number | slitting position (serve as identification information) | determination |
|---|---|---|
| #A0001 | 400 | $x\alpha$ |
| | 220 | $x\beta$ |
| | 400 | $x\alpha$ |
| | 405 ※ | $x\beta$ |
| | 400 | $x\alpha$ | example of slitting position information

INFORMATION STORING, READOUT AND CALCULATION SYSTEM FOR USE IN A SYSTEM FOR CONTINUOUSLY MANUFACTURING LIQUID-CRYSTAL DISPLAY ELEMENTS, AND METHOD FOR PRODUCING THE SAME

CROSS-REFERENCE TO RELATED APPLICATIONS

The present application claims priority to Japanese patent application number 2009-236091, filed on Oct. 13, 2009, which is incorporated by reference in its entirety.

TECHNICAL FIELD

The present invention relates to a system and method for continuously manufacturing liquid-crystal display elements. More particularly, the present invention relates to a system and method for continuously manufacturing liquid crystal elements by laminating sheets of polarizing composite film to respective ones of liquid crystal panels, the sheet of polarizing composite film being formed to have a dimension corresponding to a dimension of a liquid crystal panel. More specifically, the present invention relates to an information storage-readout-calculation system adapted for use in a continuous system for manufacturing liquid-crystal display elements, and comprising information storage medium for storing information associated with defects existing in a continuous optical film laminate and detected through a preliminary inspection, a roll of a continuous optical laminate which has been subjected to the preliminary inspection and provided with identification indicia, and a slitting position calculation means for determining slitting positions based on defect information read out from the information storage medium.

BACKGROUND ART

Taking a widescreen television having a diagonal screen size of 42 inches as an example, a liquid-crystal panel W therefor comprises a layered liquid-crystal panel which includes a pair of rectangular-shaped glass substrates each having a size of about 540 to 560 mm in length×about 950 to 970 mm in width×about 0.7 mm (700 µm) in thickness, and a liquid-crystal layer having a thickness of about 5 µm provided with a transparent electrode, a color filter etc., and sandwiched between the glass substrates, as shown in FIG. 1. The thickness of the liquid-crystal panel W itself is about 1.4 mm (1400 µm). The liquid-crystal display element is typically manufactured by laminating a polarizing composite film sheet 11" including a polarizer and a protective film to each of the front (viewing side) and back (backlight side) sides thereof. The polarizing composite film sheet 11" is formed, for example, to have a dimension shown in FIG. 1 from a polarizing composite film 11 which is provided in the form of a flexible optical film laminate 10 having a laminate structure.

For a liquid-crystal display element to function, the direction of orientation of liquid-crystal molecules and the direction of polarization of the polarizer are closely related each other. In liquid-crystal display element technologies, LCDs (Liquid-crystal Display) using a TN (Twisted Nematic) type liquid-crystal have first been put into practical use, and then LCDs using a VA (vertical Alignment) type liquid-crystal, an IPS (Inplane Switching) type liquid-crystal etc., have been put into practical use. Although a detailed technical explanation is omitted, in an LCD using such TN-type liquid-crystal panel, liquid-crystal molecules are provided between two upper and lower orientation films having respective rubbing directions on the inner surfaces of glass substrates of the liquid-crystal panel. This means that the liquid-crystal molecules are twisted by 90 degrees along the optical axis, so that when a voltage is applied, the liquid-crystal molecules are aligned in a direction perpendicular to the orientation of films. However, in the case where the LCD is designed to allow images as seen from right and left sides of a display screen as those view directly in front of the display screen, the direction of rubbing on the orientation film at the viewing-side must be 45 degrees (the rubbing direction of the other orientation film is 135 degrees). It is therefore necessary that sheets of the polarizing composite films to be laminated respectively on the front and back sides of the liquid-crystal panel must have polarizers respectively oriented in directions inclined by 45 degrees with respect to a lengthwise or widthwise direction of the display screen so as to conform to the rubbing directions.

Therefore, it is required that the optical film laminate is punched out or cut into a rectangular-shaped sheet having a long or short side determined in accordance with the size of the TN liquid-crystal panel, in such a manner that the long or short side inclined by 45 degrees with respect to the orientation direction of the polarizer. This procedure is described in Japanese Laid-Open Patent Publication JP 2003-161935A (Patent Document 1) or Japanese Patent 3616866 B (Patent Document 2), for example. The sheet of such rectangular shape has a width or a short side dimension which is smaller than the width of the optical film laminate. The rectangular-shaped sheets punched out or cut from the optical film laminate may be collectively referred as "individualized sheets."

In producing a liquid-crystal display element using such individualized sheets, each of the individualized sheets is punched out or cut in advance together with a separator adhered to an adhesive layer. The shaped individualized sheets are stored in a magazine in a liquid-crystal display element production process. The individualized sheets stored in the magazine are taken out and conveyed one-by-one by means of a suction conveyance unit to the lamination position for lamination with respective ones of the liquid-crystal panels W. Before being laminated to the liquid-crystal panel W, the separator releasably laminated to a formed adhesive layer is peeled from respective ones of the individualized sheets, and each of the individualized sheets is laminated to the liquid-crystal panel W via as such exposed adhesive layer. As the individualized sheets are flexible, they tend to be bowed or warped on their edges, and thus it is a serious technical impediment in lamination with liquid-crystal panels. Thus, in producing a liquid-crystal display element using individualized sheets, it has been required to adopt individualized sheets having four trimmed sides and a certain level of stiffness for less deflection or bend and which can be conveyed and laminated easily, to facilitate peeling respective ones of separators one-by-one and an accurate and swift positioning and laminating respective ones of the individualized sheets with liquid-crystal panels. For this reason, the individualized sheets have been laminated with a protective film, for example, of 40 to 80 µm thick not only to one surface but also to both surfaces of the polarizer to have stiffness induced by the thickness. During the initial period in the history of the manufacturing process of the liquid-crystal display elements, the optical film sheet or a polarizing sheet comprised in such optical film sheet was generally known as "polarizing plate" which is still used as a common name.

In the manufacturing process of TN-type liquid-crystal display elements, it is impossible to obtain finished liquid-crystal display elements simply by sequentially laminating the sheets formed in the sequential punching or cutting process to respective ones of a plurality of liquid-crystal panels in a subsequent process. This is because the sheet of the optical film laminate is cut from the web in such a manner that the sheet has a long or short side extending in a direction 45 degrees with respect to the orientation direction of the polarizer which is the longitudinal or stretching direction of the polarizer base film (i.e., with respect to the feed direction of the optical film laminate prior to the punching or cutting process), so that the sheet cannot be laminated to respective ones of the liquid-crystal panels with the orientation as it has been cut from the web. Therefore, to laminate the sheets to the liquid-crystal panel, each of the sheets need to be punched-out at an angled direction of 45 degrees from the continuous web of the optical film laminate having a width greater than a long side of the liquid-crystal panel with respect to the lengthwise direction of the optical film laminate, using, for example, a die wider than a long side of the liquid-crystal panel, and fed to the lamination station where the polarizing sheets are laminated with the liquid-crystal panels, as seen in the Patent Document 1 or 2. Alternatively, the continuous optical film laminate in use needs to be an elongated optical film laminate preliminarily punched or cut from the continuous web of the optical film laminate having a substantially large width in a direction 45 degrees inclined with respect to the lengthwise direction, or an elongated optical film laminate formed with a plurality of formed sheets connected into a continuous film configuration. At any rate, the above methods do not provide any noticeable improvement over the method of using individualized sheets.

The Patent Document 3 is the Japanese Patent Publication No. 62-14810B which discloses, prior to the VA-type liquid-crystal and the IPS-type liquid-crystal being brought into practical use, an apparatus to produce a liquid-crystal panel element. The apparatus is considered to be a type of labeler unit which produces an LCD using the TN-type liquid-crystal. There is taught to provide an optical film laminate in the form of an elongated continuous optical film laminate having substantially large width and slit it in a direction 45 degrees oblique to the stretching direction of the polarizing composite film with a width corresponding to the width of the liquid-crystal panel. Alternatively, a film-like elongated optical film laminate sheet may be formed by longitudinally connecting a plurality of optical film laminate sheets. Therefore, the method taught by the Patent Document 3 cannot be applied directly to a manufacturing process adapted to perform steps of continuously providing a plurality of polarizing composite film sheets from a continuous optical film laminate and laminating the respective sheets to respective ones of the liquid-crystal panels comprising VA-type or IPS-type liquid-crystal.

Automation of manufacturing process for liquid-crystal display elements using individualized sheets is disclosed, for example, in the Japanese Laid-Open Patent Publication JP 2002-23151A (Patent Document 4). Flexible individualized sheets tend to be bowed or warped due to curves or distortion of their edges, and thus it is a serious technical impediment to accuracy and speed in registration and lamination with liquid-crystal panels. Thus, it will be understood that the individualized sheet is required to have a certain level of thickness and stiffness to facilitate registration and lamination with liquid-crystal panels typically in transportation under suction. For example, the disclosures in the Japanese Laid-Open Patent Publication JP 2004-144913A (Patent Document 5), Japanese Laid-Open Patent Publication JP 2005-298208A (Patent Document 6) or Japanese Laid-Open Patent Publication JP 2006-58411A (Patent Document 7) disclose measures for addressing such technical problems.

In contrast to TN-type liquid-crystal panels, the VA-type and IPS-type liquid-crystal panels are not designed to arrange liquid-crystal molecules in twisted orientations. Thus, in the case of the liquid-crystal display element using these types of liquid-crystal panels, there is no need to have the polarization axis of the polarizing sheet oriented at 45 degrees in view of viewing angle characteristics inherent to the orientation of the liquid-crystal. Each of these liquid-crystal display elements using these liquid-crystal panels is formed by applying polarizing sheets to the opposite sides of the liquid-crystal display panel oriented with their polarization axes crossed at 90 degrees crossing angle. In the case of the VA-type and IPS-type liquid-crystal panels, with respect to the technical view point of symmetry of the viewing angle characteristics and visibility, maximum contrast can be obtained along the direction of the polarizing axis of the polarizing sheet, so that it is preferable that the sheets have polarizing axes oriented in parallel with the longitudinal or transverse direction of the liquid-crystal panel. Thus, it will be understood that these sheets to be applied to the liquid-crystal panel has a feature that the continuous optical film laminate including a polarizing composite film which has been subjected to a longitudinal or transverse stretching can be continuously fed out from a roll and cut along transverse lines with respect to the feed direction of the continuous optical film laminate to sequentially produce rectangular polarizing sheets having the same width as the optical film laminate width.

Because of the improved viewing angle characteristics, for liquid-crystal used in a display element for widescreen televisions, the VA-type liquid-crystal or the IPS-type liquid-crystal are more widely adopted than the TN type. In view of such trend in environments of technical developments, proposals to enhance the manufacturing efficiency using these types of liquid-crystal panels have been made such as the one described in Japanese Laid-Open Patent Publication JP 2004-361741A (Patent Document 8). This patent discloses steps of continuously feeding a continuous optical film laminate, cutting the continuous optical film laminate in conformity with the size of a liquid-crystal panel and sequentially laminating a plurality of optical film sheets which have been produced by the cutting step to respective ones of a plurality of the liquid-crystal panels.

However, the mainstream of manufacture of liquid-crystal display elements is still based on the manufacturing technology utilizing individualized sheets, due to the following technical problems. In manufacturing liquid-crystal display elements, a critical technical challenge is to detect any defect which may otherwise be retained in the display elements to be formed, and to prevent any defective product from being produced. Most of the product defects primarily arise from defects in the polarizing composite film contained in the continuous optical film laminate. However, it is not practical to provide the continuous optical film laminate after completely removing all defects contained in individual films which are to be laminated together to form the optical film laminate, because it is extremely difficult to produce a defect-free continuous optical film laminate under existing circumstances. To maintain quality of display elements, it is not permitted to use a polarizing composite film sheet having visible flaws or defects for a sheet for television display element even if such a flaw or defect is small. Given that the long side dimension of a polarizing sheet formed from the polarizing composite film is about 1 m, if a defective region cannot be preliminarily removed, 20 to 200 defective liquid-crystal display elements out of 1,000 products will be produced.

Proposals relating to preliminary inspection apparatus for a polarizing composite film have previously been made, as disclosed, for example, in Japanese Patent No. 3974400B (Patent Document 9), Japanese Laid-Open Patent Publications JP 2005-62165A (Patent Document 10) and JP 2007-64989A (Patent Document 11) for improving the production efficiency of manufacturing the individualized sheets. These proposals have disclosed technical means essential to improving yield in the manufacture of such individualized sheets.

Further, Japanese Laid-Open Patent Publications JP 2007-140046A (Patent Document 12) discloses a method comprising the steps of exposing a polarizing composite film having an adhesive layer by peeling a carrier film included in the continuous optical film laminate continuously fed out from a roll of continuous optical film laminate, detecting a defect or defects present in the polarizing composite film, punching only normal regions of the polarizing composite film in rectangular shape, appropriately avoiding defective regions, and conveying the punched normal polarizing sheets to the lamination position for lamination with the liquid-crystal panels by other conveying medium. It should however be noted that this process is not the one which makes it possible to feed the normal optical film sheets formed from a continuous optical film laminate to the lamination position for lamination with the liquid-crystal panel by means of the carrier film. This technique is a method for once laminating the cut individualized sheets to other conveying medium before conveying to the lamination position with the liquid-crystal panels, so this technique is not beyond the individualized sheet manufacturing system of liquid-crystal display element.

Japanese Laid-Open Patent Publications JP 2009-061498A (Patent Document 13) discloses a method for laminating the sheets of the optical film laminate with the liquid-crystal panels and an apparatus therefor. This invention contains an innovative proposal allowing for shifting from a liquid-crystal display element manufacturing system designed to carry a plurality of preliminary formed individualized sheets in the manufacturing process of the liquid-crystal display element, and laminate the individualized sheets one by one to respective ones of a plurality of liquid-crystal panels, to a continuous manufacturing system for liquid-crystal display element designed to continuously form a plurality of optical film sheets and directly laminate the formed sheets to respective ones of a plurality of liquid-crystal panels.

However, the method and system disclosed cause not only substantial complexity in the entire system for laminating but also an increase in the number of steps and difficulty in control for each step, and thus causes reduction in the manufacturing speed.

The present invention has been made based on the aforementioned prior proposals and through intensive researches and considerations for enabling a continuous manufacturing of liquid-crystal display elements and significantly enhancing product accuracy and manufacturing speed, and drastically improving manufacturing yield, in the manufacture of liquid-crystal display elements.

The prior art documents referred to in the above descriptions are listed below.

Patent Document 1: Japanese Laid-Open Patent Publication JP 2003-161935A
Patent Document 2: Japanese Patent No. 3616866B
Patent Document 3: Japanese Patent Publication 62-14810B
Patent Document 4: Japanese Laid-Open Patent Publication JP 2002-23151A
Patent Document 5: Japanese Laid-Open Patent Publication JP 2004-144913A
Patent Document 6: Japanese Laid-Open Patent Publication JP 2005-298208A
Patent Document 7: Japanese Laid-Open Patent Publication JP 2006-58411A
Patent Document 8: Japanese Laid-Open Patent Publication JP 2004-361741A
Patent Document 9: Japanese Patent No. 3974400B
Patent Document 10: Japanese Laid-Open Patent Publication JP 2005-62165A
Patent Document 11: Japanese Laid-Open Patent Publication JP 2007-64989A
Patent Document 12: Japanese Laid-Open Patent Publication JP 2007-140046A
Patent Document 13: Japanese Laid-Open Patent Publication JP 2009-061498A

DISCLOSURE OF THE INVENTION

Problem to be Solved by the Invention

The VA-type and IPS-type liquid-crystal panels are advantageous over TN-type liquid-crystal panels from the viewpoint of manufacture in that there is no restriction in the VA and IPS-types that two polarizing sheets are required to be laminated to respective ones of front and rear surfaces of the liquid-crystal panel in 45 degrees oblique with respect to the polarization axis of the polarizing sheet on the respective sides of the liquid-crystal display element, as experienced in the manufacture of TN-type liquid-crystal panels, due to the viewing angle characteristics inherent to the orientation of the liquid-crystal. Therefore, it is possible to carry out a process for continuously manufacturing liquid-crystal display elements using the VA-type and IPS-type liquid-crystal panels, while feeding a continuous optical film laminate, by continuously laminating the polarizing composite film sheets prepared by cutting the optical film laminate in the transverse direction with respect to the feed direction of the optical film laminate with the respective ones of a plurality of the liquid-crystal panels. In addition, during the feed of the optical film laminate, if normal polarizing sheets having no defect and defective or defect-containing polarizing sheets having defects detected through the preliminary inspection of a continuous polarizing composite film are being cut out, and if only the normal polarizing sheets are laminated to respective ones of a plurality of liquid-crystal panels to make liquid-crystal display elements, without interrupting the feed of the optical film laminate, it becomes possible to obtain enhanced product accuracy and manufacturing speed as well as significantly improved production yield in the manufacture of liquid-crystal display elements.

It is therefore an object of the present invention to provide a method and system for continuously laminating only the normal polarizing sheets to the respective ones of a plurality of the liquid-crystal panels by continuously cutting out each of defective polarizing sheets having defects detected through a preliminary inspection and normal polarizing sheets having no defect, while feeding an inspected continuous optical film laminate (hereinafter referred as "inspected continuous optical film laminate") comprising a continuous polarizing composite film with an adhesive layer and a continuous carrier film releasably laminated to the adhesive layer to the lamination position without interrupting the feed of the inspected continuous optical film laminate, and thereby obtaining enhanced product accuracy and manufacturing speed as well as significantly improved production yield in the manufacture of liquid-crystal display elements.

Means for Solving the Problem

The above described object can be achieved by providing a configuration comprising an information storage medium for storing information relating to defects detected through a preliminary inspection of a continuous polarizing composite film included in a continuous optical film laminate, a roll of a continuous optical film laminate being inspected and provided with identification means or indicia which may be of visible or invisible but machine readable form, and a slitting position calculation means for determining slitting positions based on defect information read out from the information storage medium in response to reading out of the identification means provided to the roll.

In one aspect of the present invention, there is provided an information storage-readout-calculation system adapted for use in a manufacturing system for continuously manufacturing liquid-crystal display element by laminating sheets of polarizing composite film on a continuous optical film laminate to respective ones of a plurality of liquid-crystal panels, the continuous optical film laminate comprising a continuous polarizing composite film with an adhesive layer and a continuous carrier film releasably laminated to the adhesive layer, the continuous optical film laminate having a width corresponding to either of a long or short side of the liquid-crystal panel, the system comprising an information storage medium for storing information of position of at least one defect detected through a preliminary inspection of the continuous polarizing composite film included in the continuous optical film laminate, a roll of a continuous inspected optical film laminate being provided with at least one identification means or indicia for identifying the continuous inspected optical film laminate, and a slitting position calculation means for determining a defective-polarizing-sheet slitting position and a normal-polarizing-sheet slitting position by using the position information readout from the information storage medium based on the at least one identification means and length measurement data calculated based on a feed length of the continuous inspected optical film laminate fed out from the roll, the defective-polarizing-sheet slitting position and the normal-polarizing-sheet slitting position defining positions of the defective or defect-containing polarizing sheet having at least one defect and the defect-free polarizing sheet having no defect respectively, whereby, in the manufacturing system of liquid-crystal display element, allowing for defining normal polarizing sheets by forming slit lines in the continuous inspected optical film laminate in a transverse direction with respect to the feed direction of the continuous inspected optical film laminate at a side opposite to the continuous carrier film to a depth reaching a surface of the carrier film adjacent to the adhesive layer based on the defective-polarizing-sheet slitting position and the normal-polarizing-sheet slitting position.

According to one embodiment of the present invention, the continuous inspected optical film laminate further comprises a continuous surface-protection film releasably laminated to a surface opposite to the adhesive layer of the continuous polarizing composite film.

According to another aspect of the present invention, there is provided a method for producing an information storage-readout-calculation system adapted for use in a manufacturing system for continuously manufacturing liquid-crystal display element by laminating sheets of polarizing composite film on a continuous optical film laminate to respective ones of a plurality of liquid-crystal panels, the continuous optical film laminate comprising a continuous polarizing composite film with an adhesive layer and a continuous carrier film releasably laminated to the adhesive layer, the continuous optical film laminate having a width corresponding to either of a long or short side of the liquid-crystal panel, the method comprising; a step of manufacturing a roll of a continuous inspected optical film laminate provided with at least one identification means, the step comprising; manufacturing a continuous polarizing composite film having a continuous protective film laminated to at least one surface of the surfaces of a continuous polarizer, detecting at least one defect in the continuous polarizing composite film through a preliminary inspection of the continuous polarizing composite film, manufacturing a continuous inspected optical film laminate by releasably laminating a continuous carrier film to the adhesive layer of the continuous polarizing composite film, generating at least one identification means or indicia for identifying the continuous inspected optical film laminate and providing the means thereon, and winding the continuous inspected optical film laminate provided with the at least one identification means to form a roll of the continuous inspected optical film laminate, a step of storing information of position of the at least one defect detected through the preliminary inspection into a prepared storage medium to form an information storage medium being stored the position information, and a step of providing a slitting position calculation means configured to determine a defective-polarizing-sheet slitting position and a normal-polarizing-sheet slitting position by using the position information readout from the information storage medium based on the at least one identification means and length measurement data calculated based on a feed length of the continuous inspected optical film laminate fed out from the roll, the defective-polarizing-sheet slitting position and the normal-polarizing-sheet slitting position defining positions of the defective or defect-containing polarizing sheet having at least one defect and the defect-free polarizing sheet having no defect respectively.

In one embodiment of the present invention, the step of manufacturing a roll of a continuous inspected optical film laminate further comprises a step of releasably laminating a continuous surface-protection film to a surface opposite to the adhesive layer of the continuous polarizing composite film.

According to one embodiment of the present invention, the step of manufacturing a roll of a continuous inspected optical film laminate further comprises at least one of the steps of inspecting a surface of continuous polarizing composite film by means of reflected light, inspecting inside of the continuous polarizing composite film by transmitting light irradiated from a light source through the continuous polarizing composite film to detect one or more defects existing in the continuous polarizing composite film as one or more shades, or of detecting one or more defects as one or more bright spots by cross-Nichol transmission inspection designed such that the light irradiated from a light source is projected to the continuous polarizing composite film and a polarization filter, and the light which has transmitted through the continuous polarizing composite film and the polarization filter is examined, with absorption axes of the continuous polarizing composite film and polarization filter being oriented at a right angle.

According to still further aspect of the present invention, there is provided another method for producing an information storage-readout-calculation system adapted for use in a manufacturing system for continuously manufacturing liquid-crystal display element by laminating sheets of polarizing composite film on a continuous optical film laminate to respective ones of a plurality of liquid-crystal panels, the continuous optical film laminate comprising a continuous polarizing composite film with an adhesive layer and a continuous carrier film releasably laminated to the adhesive layer, the continuous optical film laminate having a width corresponding to either a long or short side of the liquid-crystal panel. The method comprises steps of manufacturing a roll of a continuous inspected optical film laminate provided with at least one identification means or indicia, by preparing a roll of continuous provisional optical film laminate including a continuous polarizing composite film with an adhesive layer and a continuous provisional carrier film releasably laminated to the adhesive layer, exposing the continuous polarizing composite film with an adhesive layer by peeling the continuous provisional carrier film from the continuous provisional optical film laminate while feeding the continuous provisional optical film laminate from the roll, detecting at least one defect in the continuous polarizing composite film having the adhesive layer thereon through a preliminary inspection of the continuous polarizing composite film, manufacturing a continuous inspected optical film laminate by releasably laminating a continuous carrier film to the adhesive layer of the continuous polarizing composite film, generating at least one identification means or indicia for identifying the continuous inspected optical film laminate and providing the means thereon, and winding the continuous inspected optical film laminate provided with the at least one identification means to form a roll of the continuous inspected optical film laminate. The method further comprising steps of storing information relating to the position of the at least one defect detected through the preliminary inspection into a prepared storage medium to form an information storage medium having the position information stored therein, providing a slitting position calculation means configured to determine a defective-polarizing-sheet slitting position and a normal-polarizing-sheet slitting position by using the position information read out from the information storage medium based on the at least one identification means or indicia and length measurement data calculated based on the feed length of the continuous inspected optical film laminate fed out from the roll, the defective-polarizing-sheet slitting positions and the normal-polarizing-sheet slitting positions defining positions of the defective or defect-containing polarizing sheet having at least one defect and the defect-free polarizing sheet having no defect, respectively.

According to one embodiment of the present invention, the continuous provisional carrier film has a transferable adhesive layer formed by subjecting one of the opposite surfaces of the film to a releasing treatment to one of the opposite surfaces, applying a solvent containing adhesive to the treated surface, and drying the film being applied the solvent.

According to one embodiment of the present invention, the continuous carrier film is subjected to a releasing treatment at the surface which is to be laminated to the exposed adhesive layer of the continuous polarizing composite film.

According to one embodiment of the present invention, the step of manufacturing a roll of a continuous inspected optical film laminate further comprises a step of releasably laminating a continuous surface-protection film to a surface opposite to the adhesive layer of the continuous polarizing composite film.

According to one embodiment of the present invention, the step of manufacturing a roll of a continuous inspected optical film laminate further comprises at least one of the steps of inspecting a surface of the continuous polarizing composite film by means of reflected light, inspecting inside of the continuous polarizing composite film by transmitting light irradiated from a light source through the continuous polarizing composite film to detect one or more defects existing in the continuous polarizing composite film as one or more shades, or, detecting one or more defects as one or more bright spots by cross-Nichol transmission inspection designed such that the light irradiated from a light source is projected to the continuous polarizing composite film and a polarization filter, and the light which has transmitted through the continuous polarizing composite film and the polarization filter is examined, with absorption axes of the continuous polarizing composite film and polarization filter being oriented at a right angle.

BRIEF DESCRIPTION OF THE DRAWINGS

FIG. 9 is a table showing a defect inspection unit, types of defect, and defect detection methods.

FIG. 11 illustrates types of identification mark for providing to a continuous inspected optical film laminate, according to one embodiment of the present invention.

FIG. 12 illustrates a method for calculating positions to form slit lines for segmenting defective regions and normal regions on a supplied continuous inspected optical film laminate.

FIG. 17 illustrates a slitting position information generated as a result of calculation by the method shown in FIG. 14.

BEST MODE FOR CARRYING OUT THE INVENTION

In the context of the description, a continuous film comprising a continuous polarizer laminated with a continuous protective film on one or both surfaces and formed with an adhesive layer on the surface to be laminated with a liquid-crystal panel is referred as "a continuous polarizing composite film," and a sheet having a rectangular shape and formed from the continuous polarizing composite film is referred as "a polarizing composite film sheet" or simply "a sheet," rather than the commonly called name "polarizing plate." In addition, when a sheet is formed from a continuous polarizing composite film having a continuous surface-protection film and a continuous carrier film attached thereto, and when this sheet has to be distinguished from "a polarizing composite film sheet", it is referred as "an optical film laminate sheet", and a sheet formed from the continuous surface-protection film or the continuous carrier film included in the continuous polarizing composite film is respectively referred as "a surface-protection film sheet" or "a carrier film sheet" respectively.

The present invention will now be described with reference to specific embodiments illustrated in the accompanying drawings.

Figure 3:
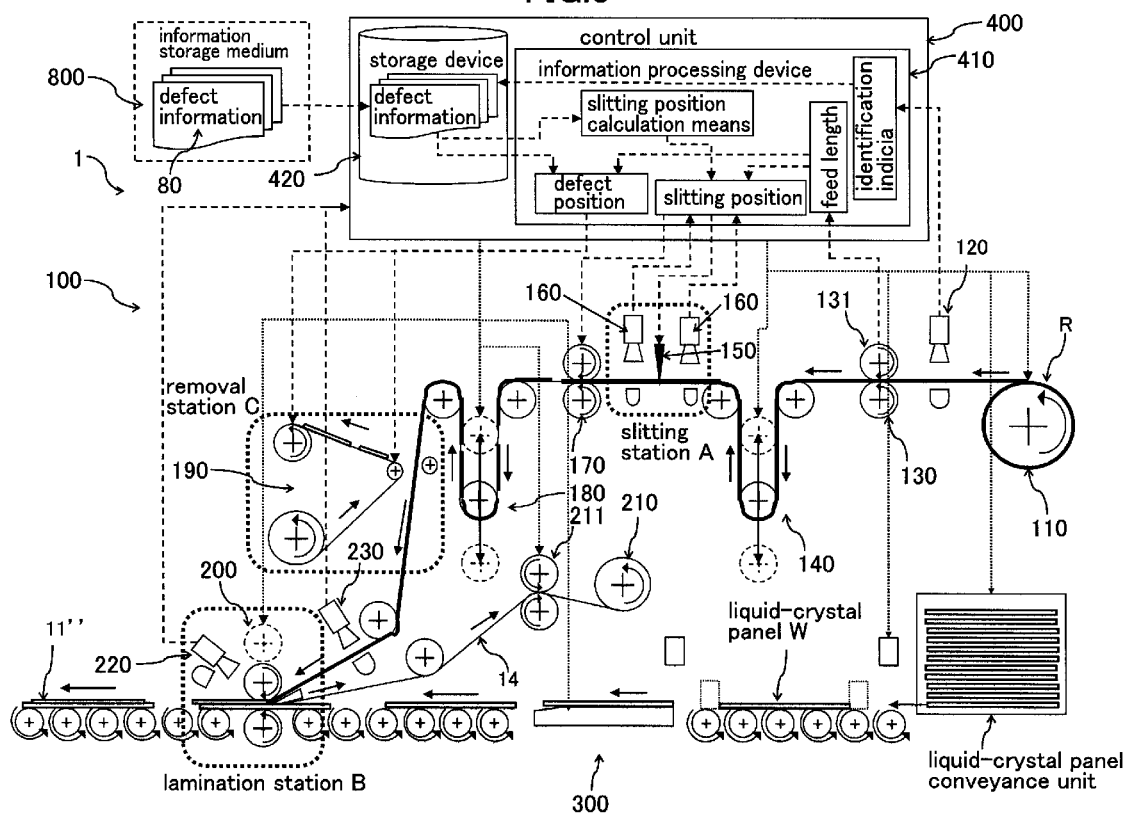
FIG. 3 is a schematic diagram showing a continuous manufacturing system for liquid-crystal display element using an information storage-readout-calculation system according to one embodiment of the present invention.

1. Configuration of System for Continuous Manufacturing Liquid-Crystal Display Elements FIG. 3 is a schematic diagram of a system 1 for continuous manufacturing liquid-crystal display elements including an information storage-readout-calculation system according to the present invention. The system 1 comprises an optical film laminate feed unit 100 equipped with a roll R of a continuous inspected optical film laminate, a liquid-crystal panel conveyance unit 300 for conveying liquid-crystal panels to be laminated with normal polarizing sheets of a polarizing composite film cut out from the continuous inspected optical film laminate, and a control unit 400 for controlling overall operations of the optical film laminate feed unit 100 and the conveyance unit 300. The roll R of the continuous inspected optical film laminate comprises a continuous polarizing composite film including an adhesive layer having a width corresponding to the width of the liquid-crystal panel and a continuous carrier film releasably laminated to the adhesive layer. It is preferable that the optical film laminate is provided with identification means 20 such as a visible or invisible but machine readable indicia which is preferably associated with a defect information 80 containing information relating to one or more defects detected through a preliminary inspection of the continuous polarizing composite film which may or may not have an adhesive layer. The identification means or indicia 20 including the defect information is stored in an information storage medium 800 in advance. The defect information 80 stored in the information storage medium 800 may include a position of defect detected in a process of manufacturing the continuous optical film laminate as will be described later. A flexible disk, a compact disk (CD), a digital versatile disk (DVD), a flash memory, or a hard disk may be used as the information storage medium. The defect information 80 is generated based on defects detected through the preliminary inspection of the continuous polarizing composite film or the polarizing composite film including an adhesive layer, and after the information is generated in a manufacturing system of the roll R, it may be directly transmitted to a storage device 420 of the continuous manufacturing system 1 through the Internet or a dedicated line without storing in the information storage medium 800. In this case, the storage device 420 functions as information storage medium according to the present invention.

The optical film laminate feed unit 100 comprises a slitting station A for slitting or cutting out polarizing composite film sheets 11" from the continuous inspected optical film laminate, a removal station C for removing defective polarizing sheets from the polarizing composite film sheets 11" being slit, and a lamination station B for laminating normal polarizing sheets to respective ones of the liquid-crystal panels. The lamination station B and the removal station C may be arranged at one position in the optical film laminate feed unit 100 as will be described later. The detail of the liquid-crystal panel conveyance unit 300 will be described later with reference to FIG. 21. The control unit 400 reads out the defect information 80 from the information storage medium 800 or the storage device 420 of the control unit 400 in response to reading of the identification means 20 by an identification means reading unit 120 and calculates slitting positions for forming slit lines on the continuous inspected optical film laminate based in the defect information.

Figure 4:
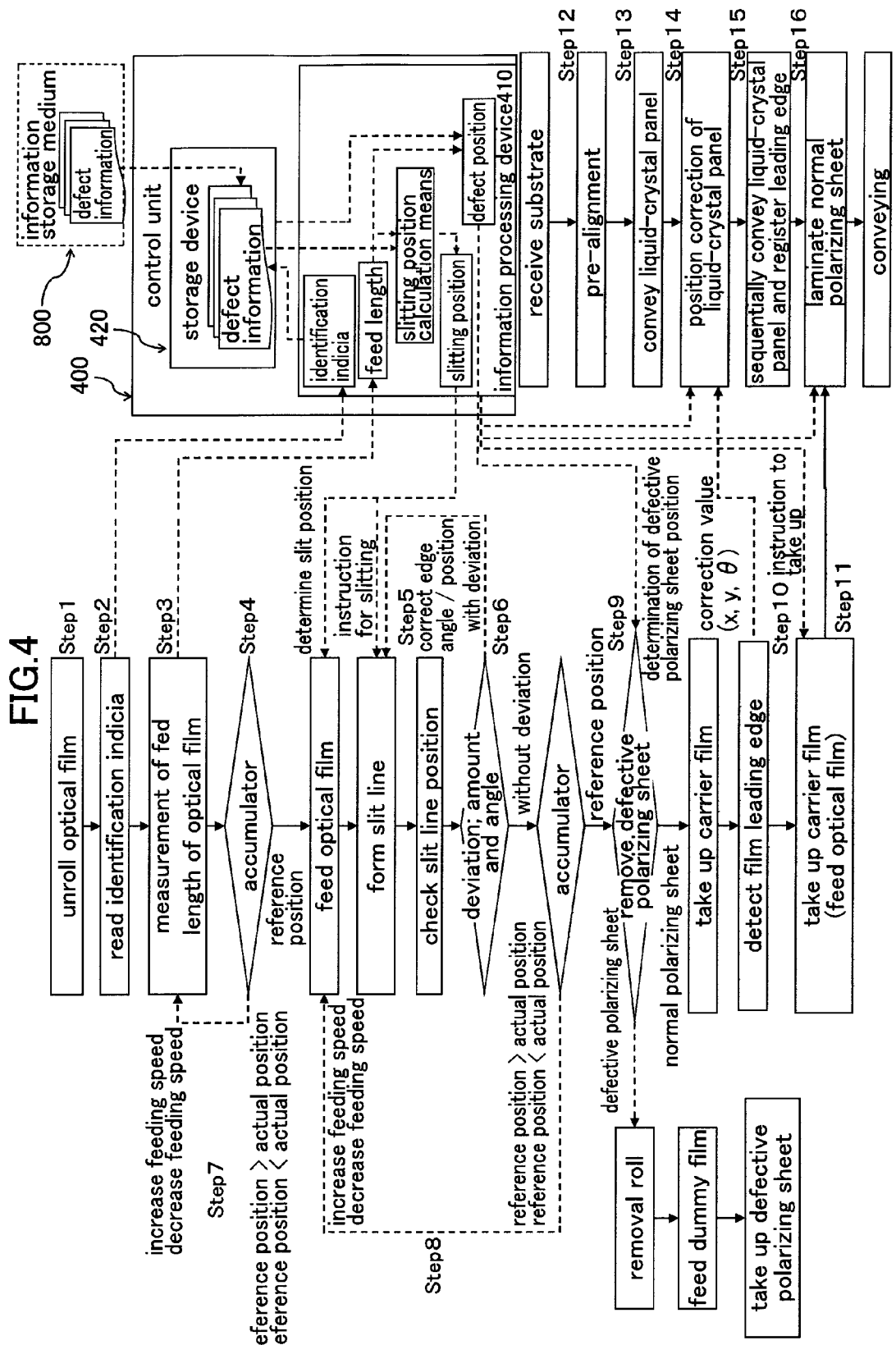
FIG. 4 is a flowchart showing manufacturing processes or process steps in the continuous manufacturing system for liquid-crystal display elements shown in FIG. 3.

The optical film laminate feed unit 100 comprises a support rack 110 for rotatably mounting the roll R of the continuous inspected optical film laminate, the identification means reading unit 120 for reading the identification means 20, a film feed unit 130 including a pair of feed rollers wherein an encoder 131 is built-in within one of the feed rollers for measuring feed length of the continuous inspected optical film laminate, a speed adjustment unit 140 including a dancing roller for providing a constant speed of film feeding, a slitting unit 150 for forming slit lines in a direction perpendicular to a feed direction on the continuous inspected optical film laminate based on a length measurement data for a feed length of the continuous inspected optical film laminate calculated by the encoder 131 and the defect information 80 read out in response to reading of the identification means 20, a slitting position check-up unit 160 for checking the position of the formed slit lines, a film feed unit 180 including a feed roller. The film feed unit 180 may comprise a speed adjustment unit 140 including a dancing roller for providing a constant speed of film feeding. The optical film laminate feed unit 100 further includes a defective polarizing sheet removal unit 190 for identifying and removing defective polarizing sheets of the polarizing composite film from the continuous carrier film, a lamination unit 200 including a pair of lamination rollers for peeling the normal polarizing sheets of the polarizing composite film being slit to a predetermined length corresponding to the liquid-crystal panel from the continuous carrier film and laminating each of the normal polarizing sheets to respective ones of the liquid-crystal panels, a carrier film take-up drive mechanism 210 for taking up the continuous carrier film, an edge detection unit 220 for detecting the leading edge of the normal polarizing sheets of the polarizing composite film, and a straight-ahead-posture or position detection unit 230 for detecting deviation of advancing position of the normal polarizing sheets of the polarizing composite film. FIG. 4 is a flowchart showing manufacturing processes or process steps in the continuous manufacturing system 1 for liquid-crystal display elements, performed by the above described units.

2. Manufacturing a Roll of a Continuous Inspected Optical Film Laminate (Configuration of a Continuous Inspected Optical Film Laminate)

Figure 2:
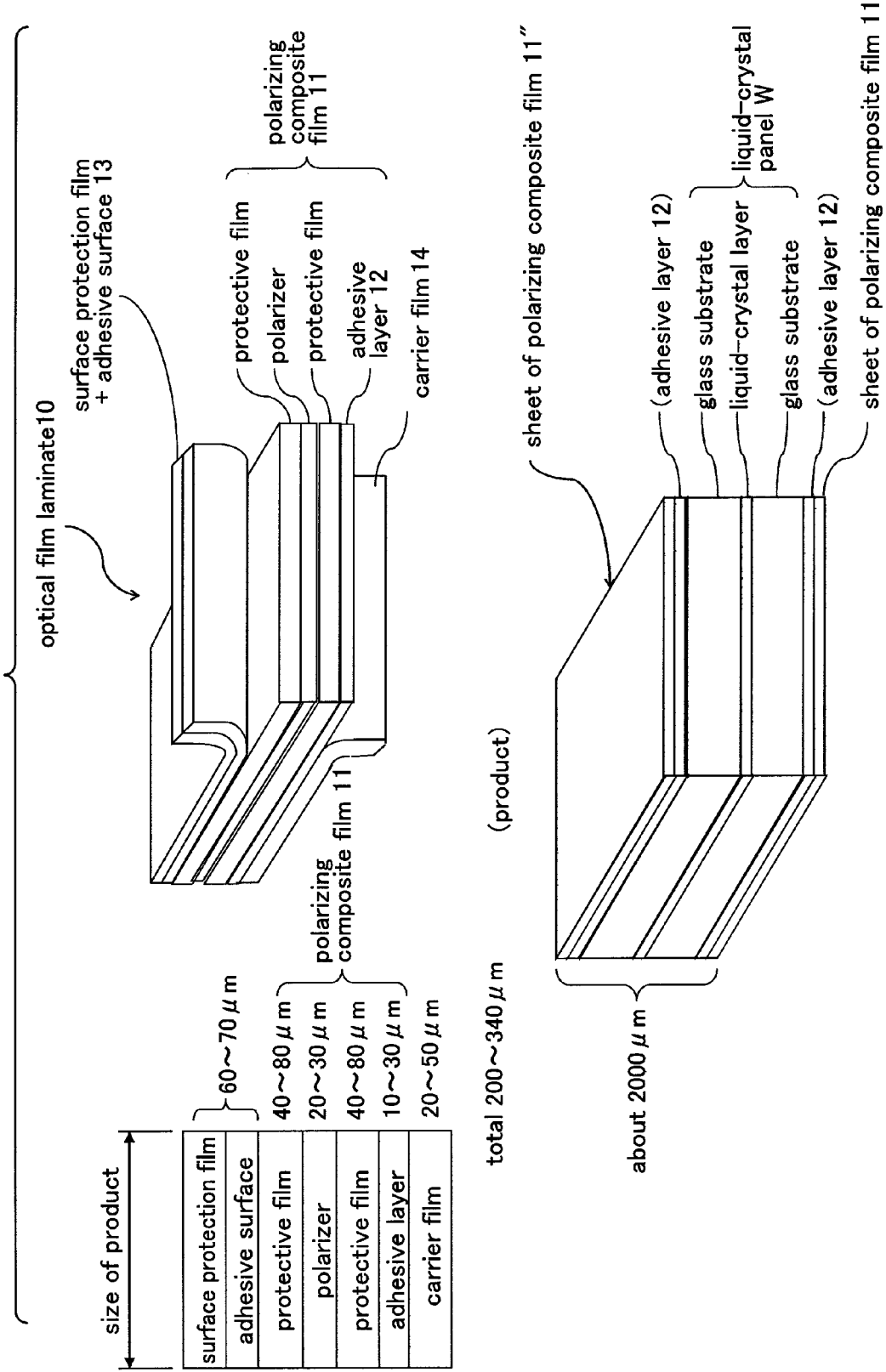
FIG. 2 illustrates the structure of a continuous optical film laminate for use in manufacturing liquid-crystal display element, and a liquid-crystal display element which a polarizing composite film sheet cut-out from the continuous optical film laminate is laminated thereto.

A continuous inspected optical film laminate mounted on the optical film laminate feed unit 100 comprises a flexible continuous optical film laminate as shown in FIG. 2 and includes a continuous polarizing composite film 11 including a continuous polarizer laminated with a transparent continuous protective film and an adhesive layer 12 formed on the surface of the polarizer to be laminated to liquid-crystal panel, a continuous surface protection film having an adhesive surface laminated to one surface of the continuous polarizing composite film 11 on which the adhesive layer 12 is not formed, and a continuous carrier film 14 releasably laminated to the adhesive layer 12 of the continuous polarizing composite film 11. In the continuous manufacturing system 1 for liquid-crystal display elements, the roll R formed by taking up the continuous inspected optical film laminate 10 is used. A continuous polarizing composite film 11' having no adhesive layer formed thereon (the reference character 11' is applied to the continuous polarizing composite film having no adhesive layer to differentiate it from the "continuous polarizing composite film 11 including the adhesive layer,") or a continuous polarizing composite film 11 including the adhesive layer is inspected for detecting any defects in advance.

There are two inspection methods for use in manufacturing the continuous inspected optical film laminate 10. One of the methods is to inspect a continuous polarizing composite film 11' being manufactured in a manufacturing process of the continuous polarizing composite film 11' where a continuous protective film is laminated with a continuous polarizer generated from PVA film. The other method is to inspect using a roll R' of a continuous provisional optical film laminate 10' including at least a prepared continuous polarizing composite film 11 including the adhesive layer and a continuous provisional carrier film 14' releasably laminated to the adhesive layer. More particularly, this is a method for inspecting the continuous polarizing composite film 11 including an exposed adhesive layer, the adhesive layer being exposed by peeling the continuous provisional carrier film 14' while unrolling the continuous provisional optical film laminate 10' from the roll R'. The continuous inspected optical film laminate 10 preferably has substantially the same width as a long side or a short side of the liquid-crystal panel to which the film 10 is to be laminated. The continuous protective film to be laminated with one or both surfaces of the continuous polarizer is preferably a transparent protection film. The continuous carrier film 14 is a releasable film which generally serves as means to protect the adhesive layer 12 of the continuous polarizing composite film 11 during manufacturing of liquid-crystal display element and is removed when normal polarizing sheets are peeled from the continuous carrier film before or at laminating to liquid-crystal panel. The carrier film 14 has a function as a carrying medium (carrier) for conveying normal polarizing composite film sheets to the lamination station B, and thus it will herein be referred as a "carrier film." The carrier film 14 may be taken up into a roll after the normal sheets are removed from the carrier film 14.

The continuous polarizing composite film 11' or the continuous polarizing composite film 11 including the adhesive layer is formed through the following process, for example. First, a PVA (polyvinyl alcohol)-based film having a thickness of about 50 to 80 μm is subjected to a dyeing treatment using iodine and a cross-linking treatment and then the resulting PVA-based film is subjected to an orientation treatment which is carried out by stretching the film in a lengthwise or widthwise direction thereof. As a result, the iodine complex is oriented in the direction parallel to the stretching direction of the PVA-based film to acquire a property of absorbing a polarized light having a plane of oscillation matching with the orientation of the iodine complex to thereby provide a continuous polarizer having absorption axes in the direction parallel to the stretching direction. In order to produce a continuous polarizer having an excellent optical property in addition to excellent uniformity and accuracy, it is desirable that the stretching direction of the PVA-based film corresponds to the longitudinal or transverse directions of the film. Generally, the absorption axis of the polarizer or the optically functional film including such polarizer is parallel to the lengthwise direction of the optically functional film, and the polarizing axis is in the widthwise direction perpendicular to the absorption axis. The thickness of the polarizer is 20 to 30 μm. Then, the continuous protective film for protection of the polarizer is laminated to each of the opposite surfaces of the formed continuous polarizer with an adhesive. Generally, a transparent TAC (triacetylcellulose)-based film having a thickness of about 40 to 80 μm is often used as the continuous protective film. From the viewpoint of reducing the thickness of the liquid-crystal display element, there may be a case where the continuous protective film is laminated with only one surface of the continuous polarizer. Finally, an acrylic adhesive layer 12 is formed on one side of the continuous polarizer having the continuous protective film laminated thereon to thereby manufacture the continuous polarizing composite film 11 including the adhesive layer. As shown in FIG. 2, the thickness of the adhesive layer is 10 to 30 μm. The thickness of the continuous polarizing composite film 11 including the adhesive layer is normally 110 to 220 μm.

One of the continuous protective films of the polarizing composite film 11 may be replaced with a phase difference film made of a cycloolefin-based polymer, a TAC-based polymer or the like and having an optical compensation function. The polarizing composite film 11' may be manufactured by providing a layer of a transparent substrate, such as a TAC-based substrate, by applying/disposing and then curing a polymer material, such as a polyester-based polymer or a polyimide-based polymer on the substrate. Further, in the case of a polarizing composite film 11' to be laminated to the backlight side of the liquid-crystal display element, it may be possible to provide an additional function by laminating a brightness enhancement film to the backlight side protective film of the polarizer. In addition, regarding the structure of the polarizing composite film 11', there have been proposed various other variations, such as a technique of laminating a TAC-based film to one of opposite surfaces of the continuous polarizer and laminating a PET (polyethylene terephthalate) film to the other surface of the continuous polarizer.

Typically, a PET-based film is used for the continuous surface-protection film 13 and the continuous carrier film 14. Both of the continuous surface-protection film 13 and the continuous carrier film 14 are so-called "manufacturing-process materials" which are to be peeled and removed prior to the final stage of the manufacturing process of the liquid-crystal display element. The continuous surface-protection film 13 is to be used for protecting the non-adhesive surface from being soiled or damaged, and the continuous carrier film 14 is used for protecting the exposed surface of the adhesive layer of the polarizing composite film 11 during the manufacturing process of the liquid-crystal display elements. The continuous provisional carrier film 14' is a film having a similar function.

One of the methods for forming an adhesive layer on the continuous polarizing composite film 11' comprises a step of laminating a continuous carrier film 14 having a transferable adhesive layer formed thereon, to the surface of the polarizing composite film 11' to be laminated to the liquid-crystal panel W. A specific transfer technique is as follows. In a manufacturing process of the continuous carrier film 14, the continuous carrier film is subjected to a releasing treatment at the surface which is to be laminated to the continuous polarizing composite film 11 at the surface which is to be laminated to the liquid-crystal panel, and then a solvent containing adhesive is applied to the treated surface and dried to form an adhesive layer on the continuous carrier film 14. Then, the continuous carrier film 14 having thus formed adhesive layer is laminated to the polarizing composite film 11', for example, while feeding the continuous carrier film 14 and the continuous polarizing composite film 11' in the same manner, so that the adhesive layer formed on the continuous carrier film 14 can be transferred to the continuous polarizing composite film 11', and the adhesive layer is formed. Alternatively, instead of the adhesive layer being formed in this manner, the adhesive layer 12 may be formed by directly applying a solvent containing adhesive to the surface of the continuous polarizing composite film 11' to be laminated to the liquid-crystal panel, and drying the same.

The continuous surface-protection film 13 typically has an adhesive surface. Unlike the adhesive layer 12 on the continuous polarizing composite film 11, the adhesive surface (not shown) must be peeled together with a sheet of the surface-protection film sheet 13 when the surface-protection film sheet 13 is peeled and removed from a polarizing sheet 11" of the polarizing composite film during the manufacturing process of the liquid-crystal display elements. The perspective view of FIG. 2 (product) shows the polarizing sheet 11" after the sheet of the surface-protection film is peeled and removed. Irrespective of whether the continuous polarizing composite film 11 has the continuous surface-protection film 13 laminated thereon, it may be possible to provide the continuous polarizing composite film 11 at the surface of the viewing side of the continuous polarizing composite film with a hard coat treatment for protecting the outermost surface of the liquid-crystal display element, and/or a surface treatment for obtaining an anti-glare effect or the like, such as an anti-glare treatment.

(Manufacturing Roll R)

The first and the second embodiments of an apparatus and a method for manufacturing a roll R of the information storage-readout-calculation system for use in the continuous manufacturing system for liquid-crystal element is explained in the followings, respectively referring to FIGS. 5 and 6, and FIGS. 7 and 8. The information storage-readout-calculation system for use in the continuous manufacturing system for liquid-crystal element comprises an information storage medium 800 for storing defect information 80 of a continuous inspected optical film laminate, a roll R of the continuous inspected optical film laminate 10 provided with an identification means 20 associated with the defect information 80, and a slitting position calculation means for determining slitting positions to be formed on the continuous inspected optical film laminate 10.

The First Embodiment

Figure 5:
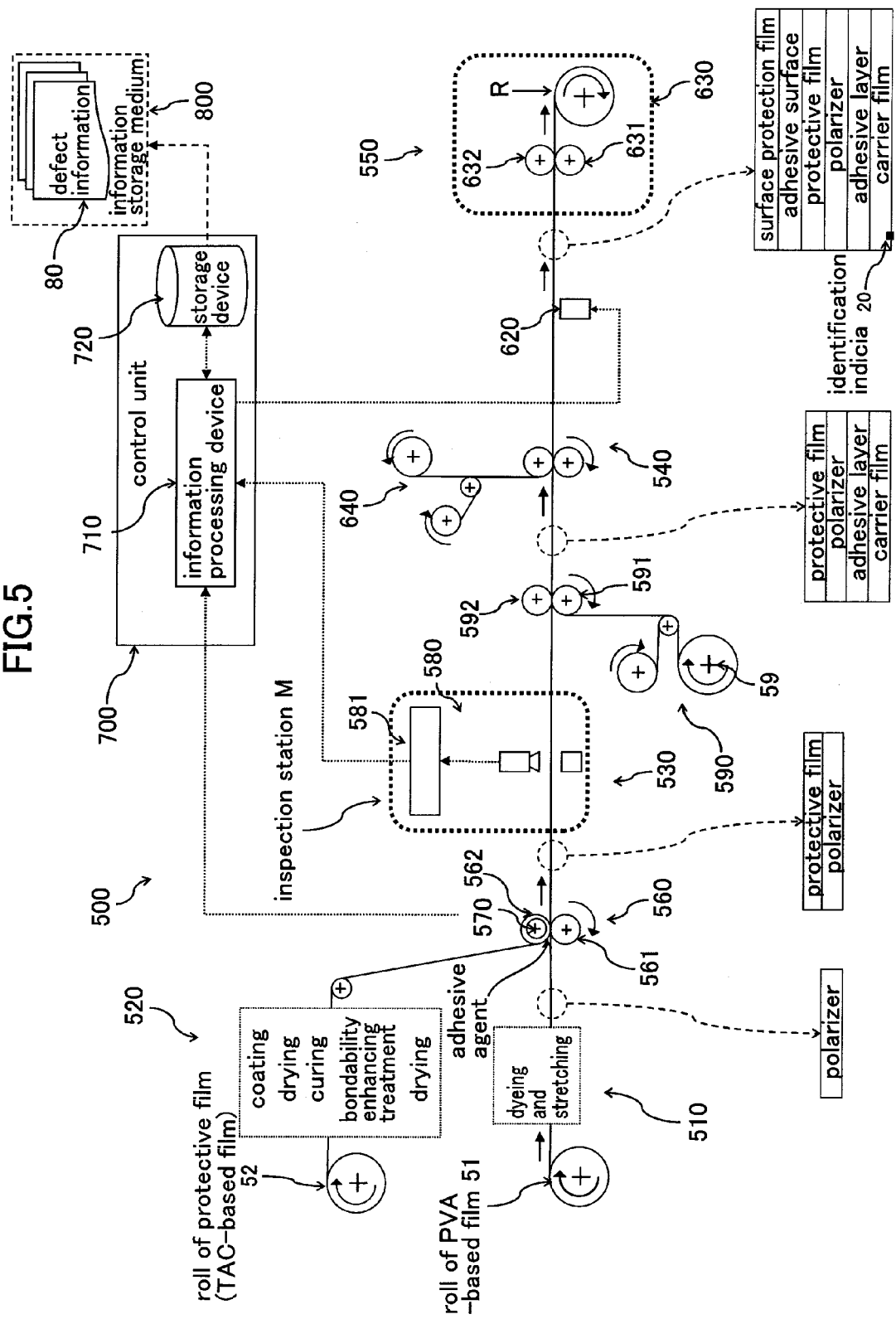
FIG. 5 illustrates a manufacturing apparatus for manufacturing a roll R of a continuous inspected optical film laminate provided with identification means associated with defect information stored in an information storage medium, according to one embodiment of the present invention.
Figure 6:
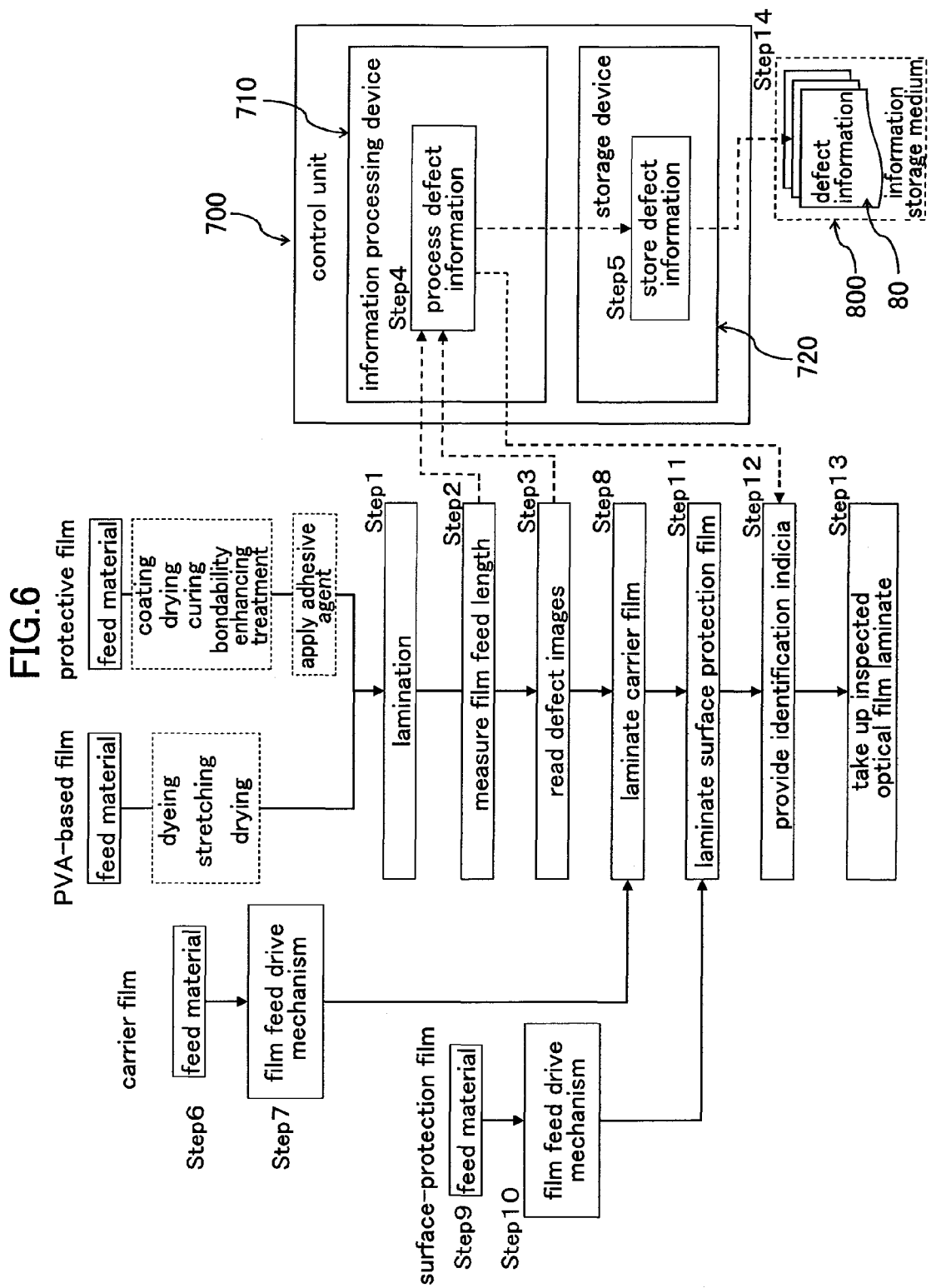
FIG. 6 is a flowchart showing manufacturing processes or process steps in the manufacturing apparatus shown in FIG. 5.

FIG. 5 is a schematic diagram of a manufacturing apparatus 500 for manufacturing a roll R of a continuous inspected optical film laminate according to one embodiment of the present invention. FIG. 6 is a flowchart showing the manufacturing processes or process steps of manufacturing a roll R of a continuous inspected optical film laminate, carried out by the manufacturing apparatus 500 shown in FIG. 5.

The apparatus 500 shown in FIG. 5 comprises a manufacturing line 530 including provisions for carrying out a step 510 for manufacturing a continuous polarizer, a step 520 for manufacturing a continuous protective film to be laminated to the continuous polarizer, and a step for manufacturing a continuous polarizing composite film 11' by laminating the continuous protective film to the continuous polarizer with an adhesive. The apparatus 500 further comprises a manufacturing line 540 for manufacturing a continuous inspected optical film laminate by laminating a continuous carrier film 14 having a transferable adhesive layer is formed thereon to one of the surfaces of the continuous polarizing composite film 11' having been inspected for defects, and releasably laminating a continuous surface-protection film 13 to the other surface of the continuous polarizing composite film 11' depending on necessity, and a manufacturing line 550 for a step of manufacturing a roll R by winding the continuous optical film laminate after providing an identification means 20. The manufacturing line 530 further comprises provisions for a step of inspecting defects inherent in the continuous polarizing composite film 11'. The manufacturing line 540 further comprises a step of providing the identification means 20 to the continuous inspected optical film laminate. The apparatus 500 further comprises a control unit 700 for controlling entire operations of the apparatus.

As shown in FIG. 5, the manufacturing line 510 handles a rotatably mounted roll 51 of PVA-based film which is adapted to provide the substrate of the continuous polarizer. The line 510 includes a sub-line for subjecting the PVA-based film to processes of dyeing, cross-linking, stretching and then drying while the film is being unrolled from the roll 51 and advanced by means of a lamination drive mechanism 560 or other drive mechanism (not shown). The manufacturing line 520 handles a rotatably mounted roll 52 of a typically transparent TAC-based film providing the substrate of the protective film, and includes a sub-line for subjecting the transparent TAC-based film being unrolled from the roll 52 by means of a lamination drive mechanism 560 or other drive mechanism (not shown), to a saponifying treatment followed by drying. The lamination drive mechanism 560 has a pair of lamination rollers 561 and 562 at the end of the manufacturing line 510 and 520, and may carry out a step of manufacturing the continuous polarizing composite film by applying an adhesive consisting primarily of a polyvinyl alcohol-based resin to an interface between the polarizer and the protective film, and drying the adhesive to bond them together through an adhesive layer having a thickness of only several μm (step 1 in FIG. 6). The lamination drive mechanism 560 includes a length or distance measurement device 570 having an encoder incorporated in one of the lamination rollers for calculating a length measurement data from a feed length measured from the leading edge of the continuous polarizing composite film 11' being manufactured, thereby allowing for measuring a feed length of the continuous polarizing composite film 11' (step 2 in FIG. 6). The lamination rollers 561 and 562 press and laminate the continuous polarizer and the continuous protective film, to form the polarizing composite film 11'. The lamination rollers 561 and 562 further coordinate with a take-up drive mechanism 630, as described later, and continuously feed-out and supply the continuous polarizing composite film 11'.

The manufacturing line 530 further includes an inspection station M for detecting defects existing in the continuous polarizing composite film 11' by inspecting the surface and inside of the continuous polarizing composite film 11' (step 3). The inspection station M includes an inspection unit 580 for detecting defects on and/or in the continuous polarizing composite film 11'. The inspection unit 580 is adapted to perform, for example, a reflection inspection, a transmission inspection, and an inspection by cross-Nichol transmission condition as shown in FIG. 9. The inspection station M may include either one of or a combination of the following three inspection units which are well-known to those in the art.

A first inspection unit is for detecting defects on a surface of the continuous polarizing composite film 11' by means of reflected light. Defects that can be inspected are defects such as surface irregularities, scratches and spots on the surface which are detectable by CCD camera, as shown in FIG. 9.

The second inspection unit is a transmission inspection unit that is designed such that light irradiated from a light source is projected perpendicular to the continuous polarizing composite film 11', and to have the light being received by an optical detection unit to detect defects existing in the continuous polarizing composite film 11' as a shade. Defects that can be detected are such as foreign substances or internal pores in the film, as shown in FIG. 9.

The third inspection unit is a defect inspection unit based on a crossed-Nichol condition. Along with the application of such defect inspection unit, the accuracy of the defect inspection of polarizing composite films has dramatically improved. Generally, manufacturers tend to use only the continuous polarizing composite film that has passed the defect inspection based on the crossed-Nichol condition for large-size liquid-crystal display elements. The inspection method is as follows. First, the target polarizing composite film 11' and the polarizing filter for it are disposed in such a manner as to allow their absorption axes to be oriented at a right angle. Then, the light emitted from the light source is projected to the polarizing composite film perpendicularly or obliquely thereto. With a polarization filter being disposed immediately before an optical detection unit so as to make an absorption axis thereof being oriented at a right angle with respect to an absorption axis of the polarizing composite film 11', the light which has passed through the polarizing composite film 11' is received by the optical detection unit to thereby detect defects existing in the polarizing composite film 11' as bright spots. As shown in FIG. 9, all defects, except surface irregularities, are detected through the third inspection unit.

The control unit 700 processes data of images of defects detected at the inspection station M to generate defect information 80 (step 4). The control unit 700 further stores the generated defect information 80 in the storage device 720 (step 5), then stores in the information storage medium 800 (step 14). The defect information 80 may be stored in a plurality of information storage media as a backup. The defect information 80, after being generated, may be directly transmitted to a storage device 420 of the continuous manufacturing system 1 for manufacturing liquid-crystal display elements through the Internet or a dedicated line without storing in the information storage medium 800. In this case, the storage device 420 functions as information storage medium according to the present invention.

The inspection unit 580 and the control unit 700 are inter-related. The inspection unit 580 comprises, for an example, an image reading unit 581 including a CCD camera. The image reading unit 581 is connected to an information processing device 710 included in the control unit 700. An image data read by the image reading unit 581 is processed in association with a length measurement data measured by a length measurement unit 570 connected to the information processing device 710. The information processing device 710 associates and processes an image data from the image reading unit 581 and the length measurement data from the length measurement unit 570 based on a feed length from the inspection reference position (normally the position of the leading edge) of the continuous polarizing composite film 11' to generate the defect information 80 relating to any defect existing in the continuous polarizing composite film 11' (step 4) for storing in the storage device 720 (step 5). The defect information 80 includes at least a position data indicating the position of a detected defect, and further, may include information related with type and size of defect.

Then, the information processing device 710 generates identification means or indicia 20 for identifying a roll of a continuous optical film laminate being manufactured from other rolls of the continuous optical film laminate. The identification means or indicia 20 is preferably associated with the defect information 80. The identification means or indicia 20 is used for reading out the defect information 80 from the information storage medium 800 or the storage device 420 during the continuous manufacturing process for manufacturing liquid-crystal display elements. The generated identification means or indicia 20 is finally applied to a manufactured continuous inspected optical film laminate (step 12) to generate the continuous inspected optical film laminate 10 provided with the identification means 20 (step 13). The identification means or indicia 20 may include information such as a manufacturing lot number and/or a length in meters of a roll, which may be associated with the defect information 80.

After completing a defect inspection of the continuous polarizing composite film 11', the adhesive layer 12 must be formed for laminating one of the surfaces of the continuous polarizing composite film 11' to liquid-crystal panel. As shown in FIG. 5, the manufacturing line 540 includes a carrier film feed unit 590 mounted with a roll 59 of a continuous carrier film 14 which an adhesive layer is transferably formed thereon in advance. The continuous carrier film 14 is in advance manufactured using a PET-based film with a thickness of 20 to 50 μm in a manufacturing line of the carrier film (not shown). In general, one of the surfaces of the PET-based film of the continuous carrier film 14 is subjected to a releasing treatment, and then a solvent containing adhesive is applied to the treated surface and dried to form a transferable adhesive having a thickness of 10 to 30 μm, and a releasable film is releasably laminated to the adhesive layer. Then, the continuous carrier film 14 is fed from the carrier film feed unit 590 while peeling the releasable film and is releasably laminated to the continuous polarizing composite film 11' by a pair of carrier film lamination rollers 591 and 592, thereby the adhesive layer formed on the continuous carrier film 14 is transferred to the continuous polarizing composite film 11' to generate the continuous polarizing composite film 11' including an adhesive layer.

The manufacturing line 540 may include a surface-protection film feed unit for laminating a continuous surface-protection film 13 having an adhesive surface on a surface opposite to the one laminated with the continuous carrier film 14 of the continuous polarizing composite film 11. The manufacturing line 540 further includes an identification means providing unit 620 for providing the identification means 20 after the continuous inspected optical film laminate 10 is manufactured by laminating the continuous surface-protection film 13 and/or the continuous carrier film 14 to the continuous polarizing composite film 11. It is preferable that position for providing the identification means 20 corresponds to the starting position of a defect inspection of the continuous polarizing composite film 11'.

The manufacturing line 550 includes an optical film laminate take-up drive mechanism 630 having a pair of take-up rollers 631 and 632 for taking up the continuous inspected optical film laminate 10 after providing the identification means 20 by the unit 620 to form a roll R (step 13). In case where the continuous protective film is laminated on both surfaces of the continuous polarizer, the system 500 may include two protection film manufacturing lines 520, 520' (the protection film manufacturing line 520' is omitted in the drawing). Further, the continuous protective film manufacturing line 520 may additionally include a treatment sub-line for, before a continuous protection film is laminated to the continuous polarizer, subjecting the surface of the protection film (non-laminated surface) to a hard coat treatment or antiglare treatment.

The Second Embodiment

Figure 7:
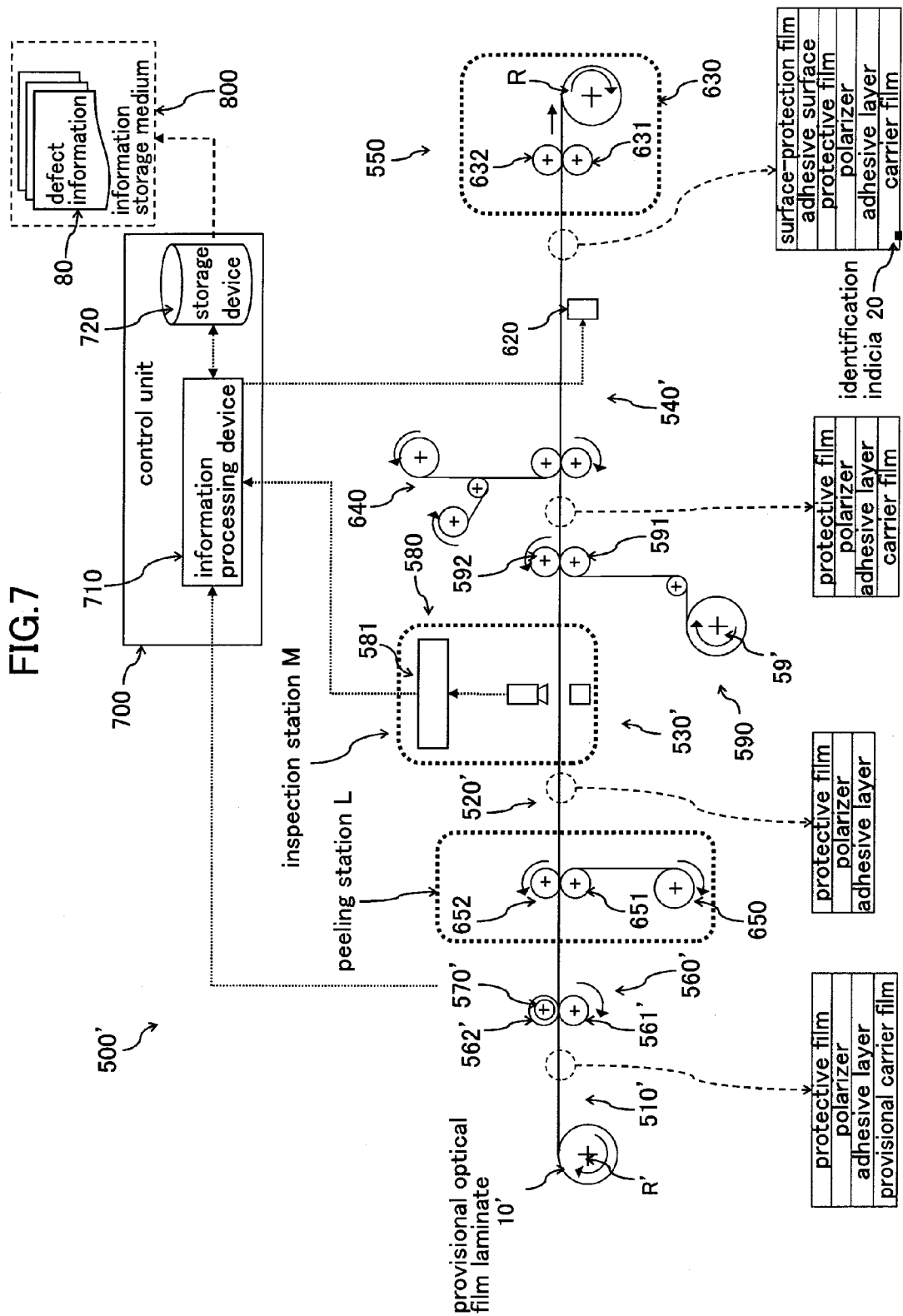
FIG. 7 illustrates a manufacturing apparatus for manufacturing a roll R of a continuous inspected optical film laminate provided with identification means associated with defect information stored in an information storage medium, according to another embodiment of the present invention.
Figure 8:
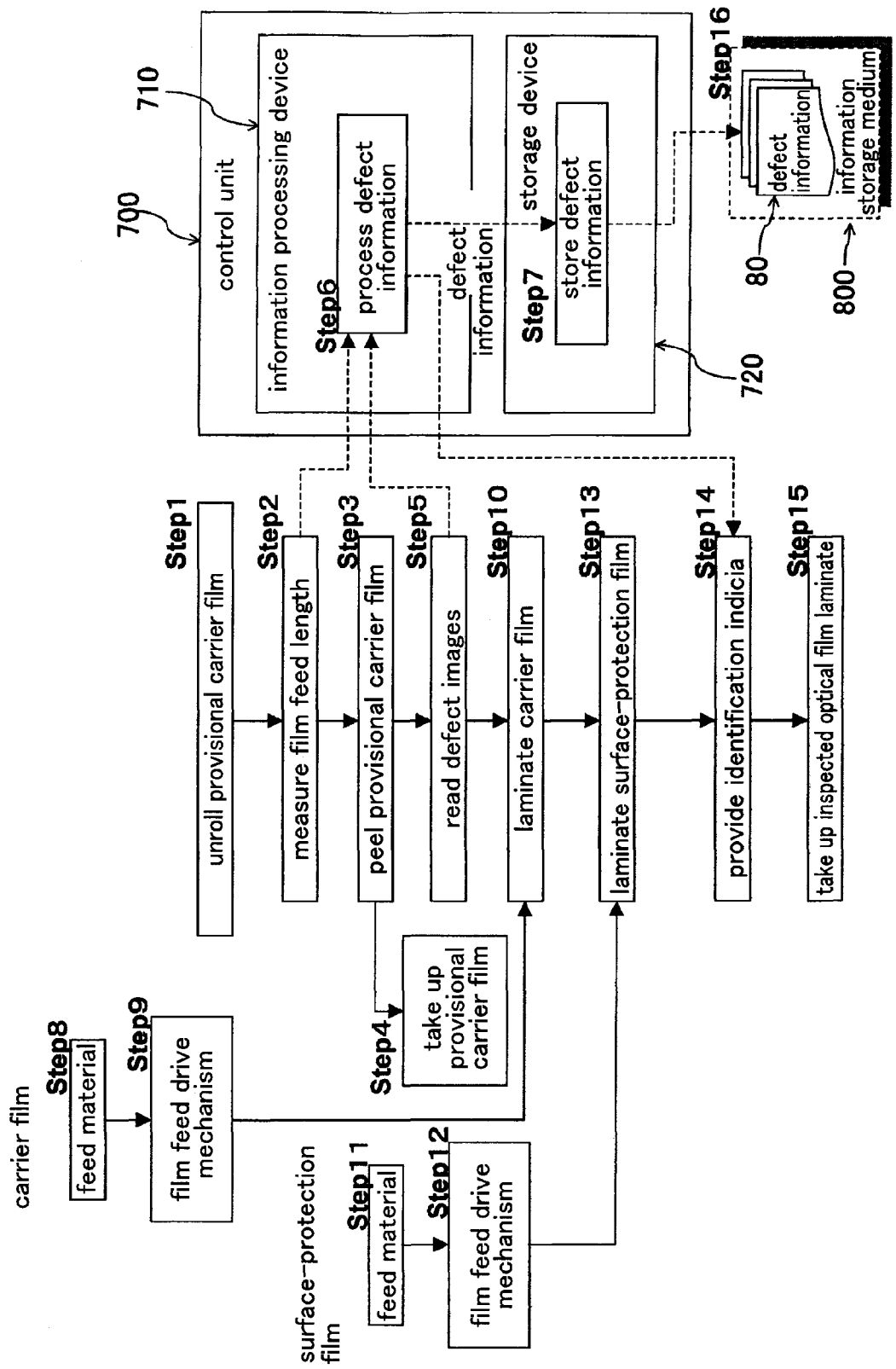
FIG. 8 is a flowchart showing manufacturing processes or process steps in the manufacturing apparatus shown in FIG. 7.

FIG. 7 is a schematic diagram of a manufacturing apparatus 500' for manufacturing a roll R of a continuous inspected optical film laminate, according to one embodiment of the present invention. FIG. 8 is a flowchart showing manufacturing processes or process steps of manufacturing a roll R of a continuous inspected optical film laminate 10 in the manufacturing apparatus 500' shown in FIG. 7.

The apparatus 500' shown in FIG. 7 is explained using the same reference numerals for the same configurations, except for the configuration different from that in the apparatus 500 of the first embodiment. In the apparatus 500', an in advance manufactured and prepared roll R' of a continuous provisional optical film laminate 10' is used. The roll R' is formed by taking up the continuous provisional optical film laminate 10' at least including the continuous polarizing composite film 11 having an adhesive layer and a continuous provisional carrier film 14' releasably laminated to the adhesive layer. The continuous polarizing composite film 11 herein disclosed has an adhesive layer formed on a continuous laminate comprising a continuous protective film laminated on a continuous polarizer, and is in the form of a continuous polarizing composite film including an adhesive layer. The continuous polarizing composite film 11 is a continuous polarizing composite film before defect inspection, i.e. defects inherent in the film are not yet detected. The continuous provisional carrier film 14' for protecting the adhesive layer is releasably laminated to the adhesive layer. Thus, the apparatus 500' comprises a provisional optical film laminate feed line 510' for feeding the continuous provisional optical film laminate 10' from the roll R' rotatably mounted on a support rack and a polarizing composite film feed line 520' for feeding the continuous polarizing composite film including an adhesive layer in an exposed-state by peeling the continuous provisional carrier film 14' from the continuous provisional optical film laminate 10'.

In the apparatus 500' of the second embodiment, the aforementioned in advance manufactured roll R' of a continuous provisional optical film laminate 10' is used. Thus, the apparatus 500' does not have a manufacturing line for a continuous polarizer or that for a continuous protective film. Further, unlike the manufacturing line 530 of the first embodiment, a step of applying an adhesive to an interface between the continuous polarizer and the continuous protective film, and drying the adhesive to bond those together is not required. Instead, there is provided the aforementioned provisional optical film laminate feed line 510' for feeding the continuous provisional optical film laminate 10' from the roll R' (step 1 shown in FIG. 8). The feed line 510' comprises a provisional optical film laminate feed drive mechanism 560' including a pair of feed rollers 561' and 562' for feeding out the continuous provisional optical film laminate 10' from the roll R' mounted on a support rack. The provisional optical film laminate feed drive mechanism 560' includes a length or distance measurement device 570' having an encoder incorporated in one of the feed rollers for calculating a length measurement data from a feed length measured from the leading edge of the continuous provisional optical film laminate 10', thereby allowing for measuring a feed length of the continuous provisional optical film laminate 10' (step 2). The feed rollers 561' and 562' cooperate with the take-up drive mechanism 630 and continuously feed-out and supply the continuous provisional optical film laminate 10'.

The provisional optical film laminate feed line 510' shown in FIG. 7 includes a peeling station L for peeling the continuous provisional carrier film 14' from the continuous provisional optical film laminate 10' by means of a provisional carrier film peeling unit 650 to expose the continuous polarizing composite film 11 including an adhesive layer for feeding. The feed line 520' feeds the continuous provisional optical film laminate 10' including a continuous provisional carrier film 14' to the peeling station L by means of the provisional optical film laminate feed unit 560'. The manufacturing line 530' carries out an inspection process wherein the continuous polarizing composite film 11 including an exposed adhesive layer is fed to an inspection station M for detecting defects existing in this film. Manufacturing of roll R of the continuous inspected optical film laminate 10 according to the second embodiment is initiated by the manufacturing line 530'.

It is preferable that a continuous provisional carrier film 14' having a transferable adhesive layer formed thereon is used in the manufacturing process of the roll R' of the continuous provisional optical film laminate 10'. This is to allow for manufacturing the continuous polarizing composite film 11 including an adhesive layer by having the adhesive layer releasably formed on the continuous provisional carrier film 14' transferred to the continuous polarizing composite film 11' when the continuous provisional optical film laminate 10' is unrolled from the roll R' and the continuous provisional carrier film 14' is peeled from the continuous provisional optical film laminate. The manufacturing line 530' also includes an inspection station M, similar to that in the apparatus 500 of the first embodiment.

In the apparatus 500, the inspection for detecting defect is conducted on the continuous polarizing composite film 11' not including an adhesive layer, however, in the apparatus 500', the inspection is made on the continuous polarizing composite film 11 including an adhesive layer which is in the exposed state. The inspection station M includes an inspection unit 580 for inspecting defects on surfaces and inside the continuous polarizing composite film 11 including an adhesive layer. The inspection unit 580 is adapted to perform, for example, a reflection inspection, a transmission inspection, and an inspection by cross-Nichol transmission condition as shown in FIG. 9. The inspection units that may be included in the inspection station M are similar to those for the first embodiment described above. The control unit 700 processes image data of defects detected at the inspection station M to generate the defect information 80 (step 6). The generated defect information 80 is stored in the information storage medium 800 via the storage device 720 (step 7 and step 16). The defect information 80 may be stored in a plurality of information storage media as a backup.

The relation of the inspection unit 580 and the control unit 700 is the same as in the apparatus 500 of the first embodiment. An image data read by the image reading unit 581 is processed in association with a length measurement data measured by a length measurement unit 570' connected to the information processing device 710. The information processing device 710 associates and processes an image data from the image reading unit 581 and the length measurement data from the length measurement unit 570' based on the feed length from the inspection position (normally the position of the leading edge) of the continuous provisional optical film laminate 10' to generate the defect information 80 relating to defects existing in the continuous polarizing composite film 11 including an adhesive layer (step 6) for storing in the storage device 720 (step 7).

Then, the information processing device 710 generates identification means or indicia 20 for identifying a roll of a continuous optical film laminate which is being manufactured from other rolls of the continuous optical film laminate. The identification means 20 is preferably associated with the defect information 80. The identification means 20 is used for reading out the defect information 80 from the information storage medium 800 or the storage device 420 during the continuous manufacturing of the liquid-crystal display elements. The generated identification means or indicia 20 is finally applied to the manufactured continuous inspected optical film laminate (step 14) to produce the continuous inspected optical film laminate 10 provided with the identification means 20 (step 15). The location where the identification means or indicia 20 is provided preferably corresponds to the position of starting the defect inspection of the continuous polarizing composite film including an adhesive layer. The identification means 20 may include information such as a manufacturing lot number and/or a length in meters of a roll, which may be associated with the defect information 80.

The manufacturing line 540' of the second embodiment includes a carrier film feed unit 590' on which a roll 59' of the continuous carrier film 14 is mounted. The continuous carrier film 14 is manufactured in a preceding process using a PET-based film with a thickness of 20 to 50 µm in a manufacturing line of the carrier film (not shown). One of the surfaces of the PET-based film is subjected to a releasing treatment and a transferable adhesive layer is not formed thereon like in the manufacturing line 540 of the first embodiment, so that a releasable film is not required. The continuous carrier film 14 is fed from the carrier film feed unit 590 and is releasably laminated to the adhesive layer of the continuous polarizing composite film 11 by means of a pair of carrier film lamination rollers 591' and 592'. Since the manufacturing line 550 of the apparatus 500' of the second embodiment has the same configuration and function as the apparatus 500 of the first embodiment, the explanation is waived herein.

Figure 10:
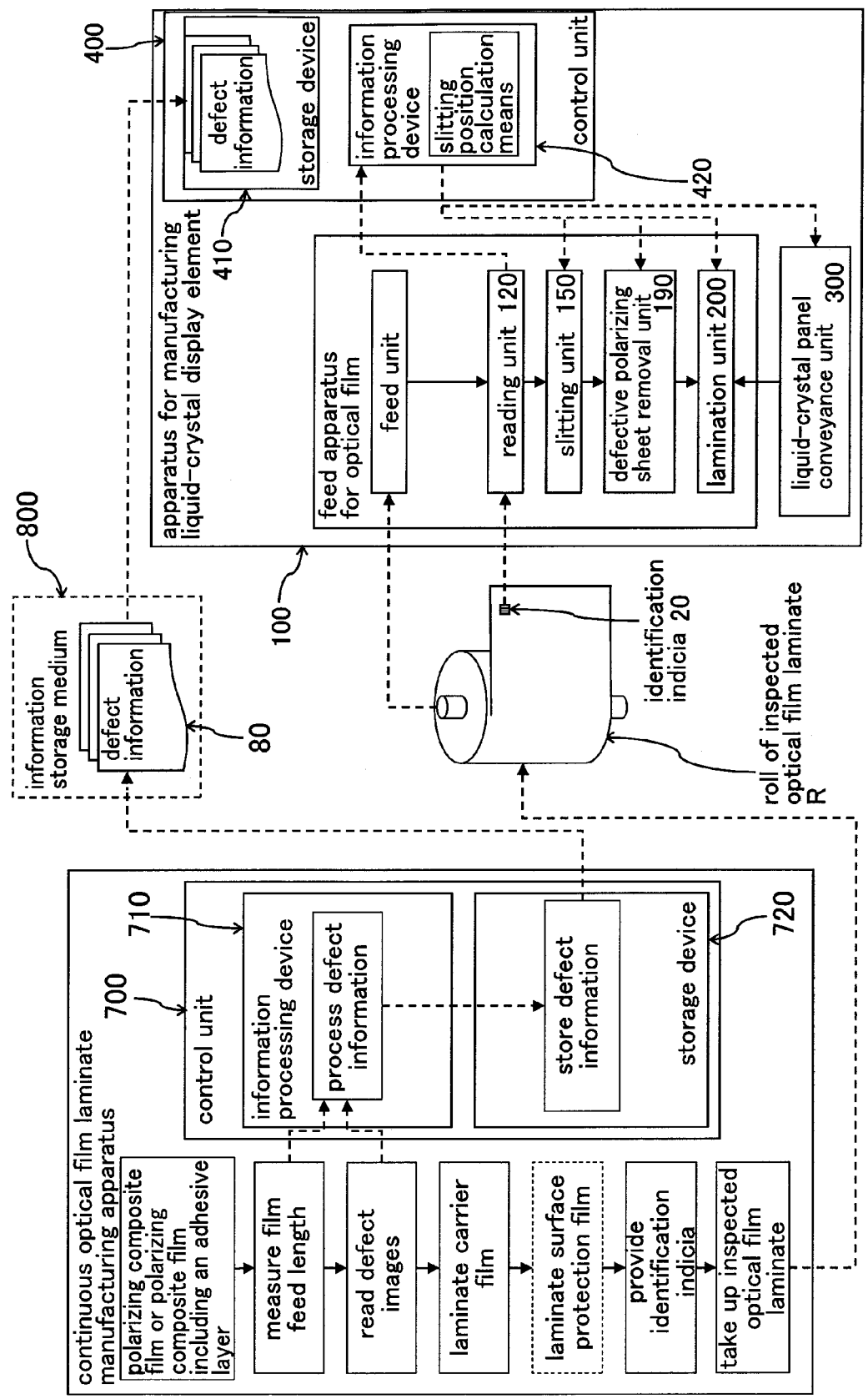
FIG. 10 illustrates an information storage-readout-calculation system including an information storage medium stored with defect information, a roll of a continuous inspected optical film laminate provided with identification means and a slitting position calculation means, according to one embodiment of the present invention.

3. Continuous Manufacture of Liquid-Crystal Display Elements Using Information Storage-Readout-Calculation System FIG. 10 illustrates an information storage-readout-calculation system according to one embodiment of the present invention. The system is designed to work with a roll R of the continuous optical film laminate 10 which has in advance been subjected to a preliminary inspection and provided with the identification means or indicia 20 generated in the apparatus shown in FIG. 5 or FIG. 7. The system includes an information storage medium and/or a storage device 410 for storing the defect information 80, and a slitting position calculation means 415 for calculating positions for forming slit lines on the continuous inspected optical film laminate 10. With reference to the flowchart of FIG. 4, a method and system for continuously manufacturing liquid-crystal display elements using the information storage-readout-calculation system according to one embodiment of the present invention will be described.

(Unrolling Continuous Inspected Optical Film Laminate 10 Provided with Identification Means 20)

The roll R manufactured as above is mounted on an unrolling unit of the optical film laminate feed unit 100 of the continuous manufacturing system 1 for liquid-crystal display element, and the continuous inspected optical film laminate 10 is unrolled from the roll R (step 1 in FIG. 4). A length measurement data of the unrolled optical film laminate 10 is calculated by an encoder 131 separately provided in the optical film laminate feed unit 100 by measuring the unrolled length of the optical film laminate (step 3 in FIG. 4). The encoder for calculating the length measurement data may be provided in the support rack 110 of the optical film laminate feed unit 100 (not shown). The length measurement data calculated by the encoder 131 is preferably stored in the storage device 420 of the control unit 400.

(Types of Identification Means 20)

FIG. 11 illustrates types of identification means or indicia which may be provided in a continuous inspected optical film laminate 10, according to one embodiment of the present invention. The identification means or indicia 20 may be either of one dimensional code, two dimensional code or IC tag, and may store identification information for specifying the continuous inspected optical film laminate 10, such as a lot number.

(Calculation of Slitting Position)

When the continuous inspected optical film laminate 10 provided with the identification means 20 (hereinafter referred simply as the continuous inspected optical film laminate 10) is continuously unrolled from the roll R, the identification means 20 is read by the identification means reading unit 120 (step 2 in FIG. 4). Then, the defect information 80 is read out from the information storage medium 800 or the storage device 420 in response to reading of the identification means 20. The slitting position calculation means 415 of the information processing device 410 uses the readout defect information 80 (specifically, a position data of defect or defects) and a length measurement data calculated by the encoder 131 to calculate a normal-polarizing-sheet slitting position to define a normal polarizing sheet Xα and a defective-polarizing-sheet slitting position Xβ to define a defective polarizing sheet Xβ.

The slitting position calculation means 415 determines information (hereinafter referred as slitting position information) of slit lines position (slitting position) to be formed on the continuous inspected optical film laminate 10 based on the defect position and the length measurement data of the continuous inspected optical film laminate 10 as follows. Slit lines are formed by the slitting unit 150 during the manufacturing process of liquid-crystal display elements, in a transverse direction with respect to the feed direction of the continuous inspected optical film laminate 10 at a side opposite to the continuous carrier film to a depth reaching a surface of the continuous carrier film adjacent to the adhesive layer. Such a slit forming method is sometimes called as "half-cut." Generated slitting position information is preferably stored in the storage device 420.

A region defined between two longitudinally adjacent ones of the slit lines, one on the upstream side and the other on the downstream side of the optical film laminate spaced apart a predetermined interval from the one on the upstream side may include defect-free normal regions and at least one defective region of a polarizing composite film. The defect free normal region has a fixed length determined by a length of a side of liquid-crystal panel to which the polarizer is to be laminated, and the defective region may typically be shorter than the fixed length. The defective region between two adjacent slit lines formed by the slitting unit 150 is specifically a defective polarizing sheet Xβ which is to be removed from the optical film laminate (actually, from the continuous carrier film 14) by the defective polarizing sheet removal unit 190. Similarly, a normal region is a normal polarizing sheet Xα to be peeled from the continuous inspected optical film laminate (actually, from the continuous carrier film 14) and laminated to one of the surfaces of liquid-crystal panel by the lamination unit 200.

Figure 13:
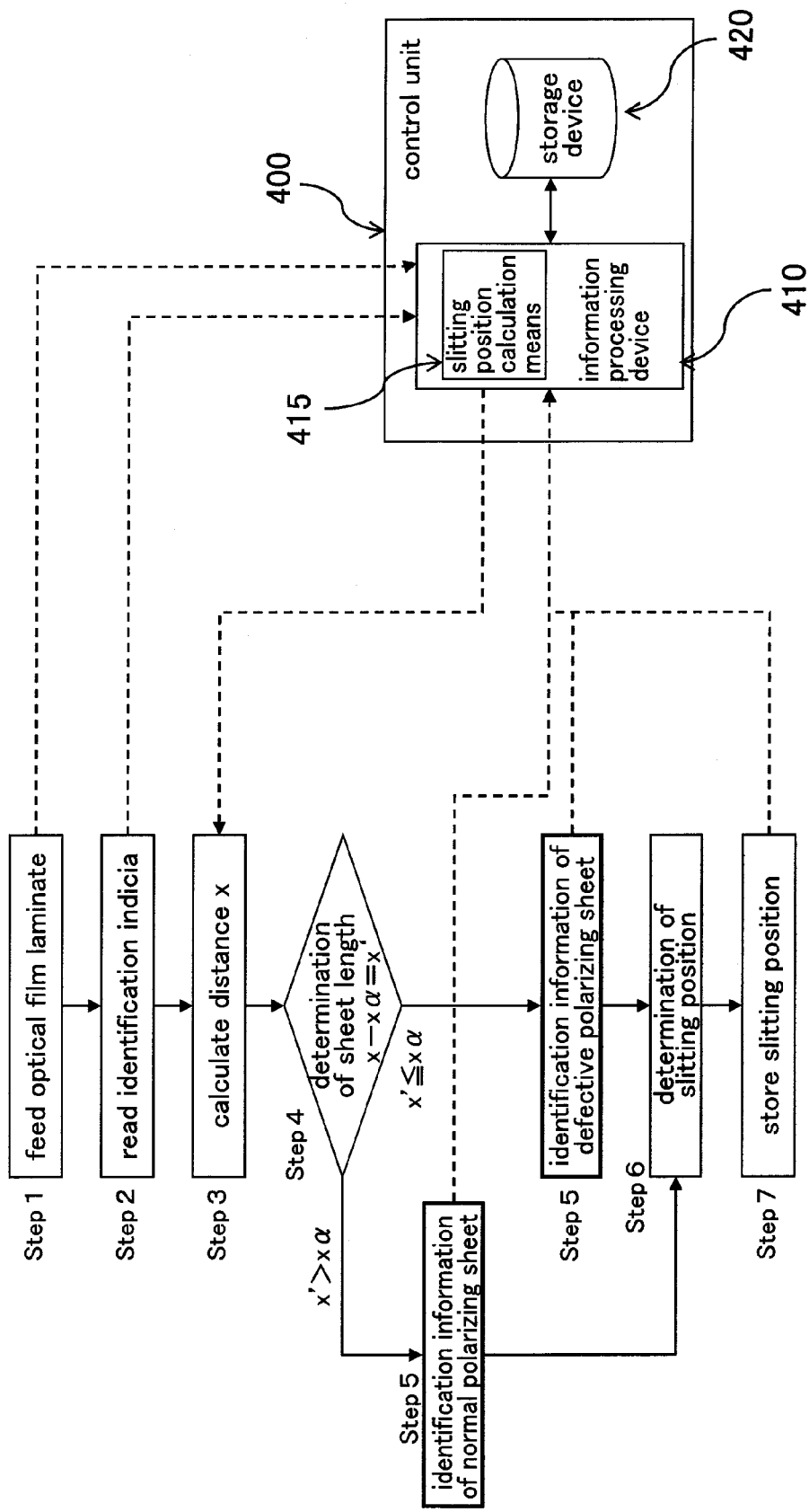
FIG. 13 is a flowchart showing a method for calculating positions to form slit lines on a supplied continuous inspected optical film laminate.
Figure 14:
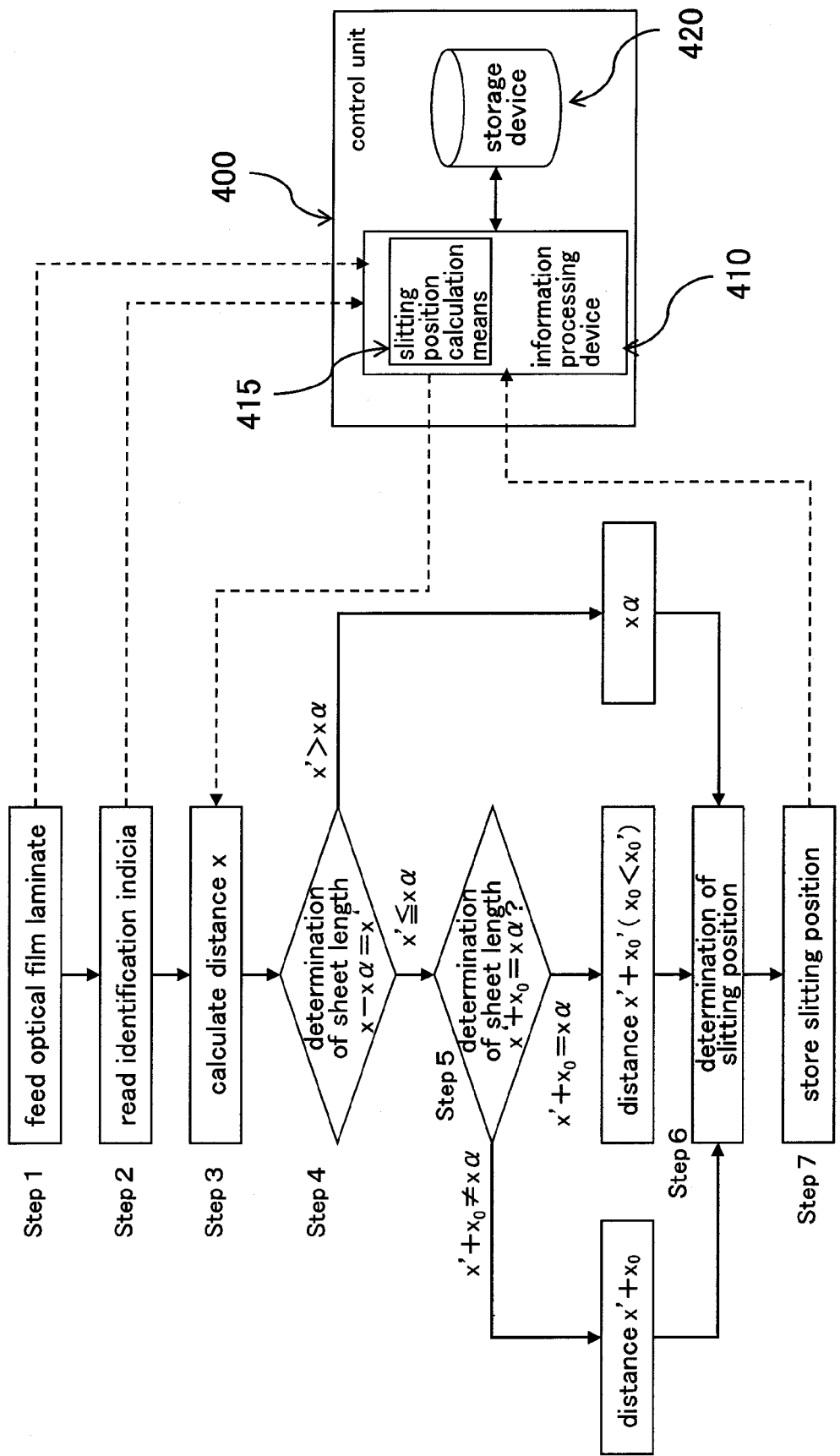
FIG. 14 is a flowchart showing another method for calculating positions to form slit lines on a supplied continuous inspected optical film laminate.
Figure 15:
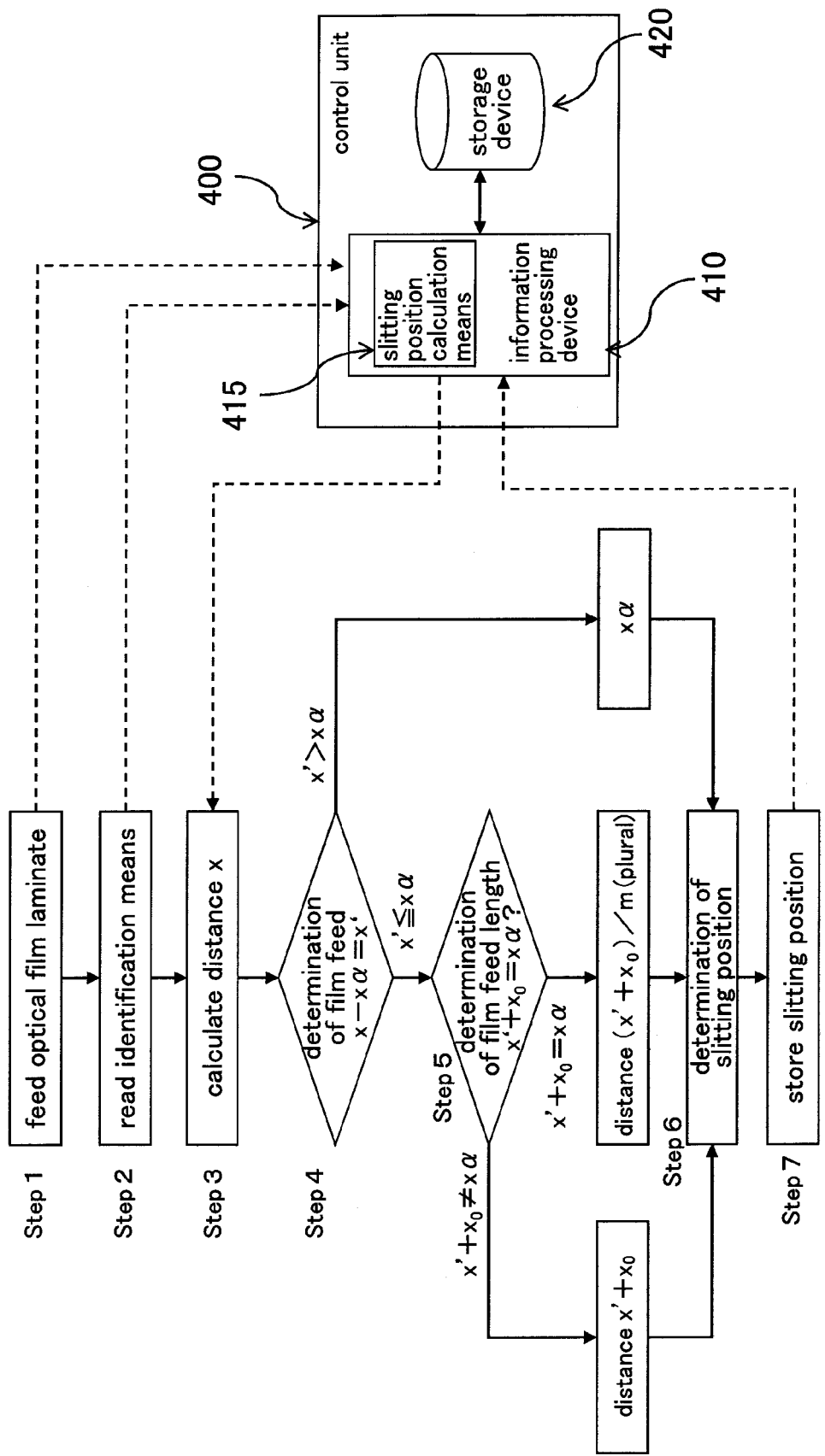
FIG. 15 is a flowchart showing yet another method for calculating positions to form slit lines on a supplied continuous inspected optical film laminate.
Figure 16:
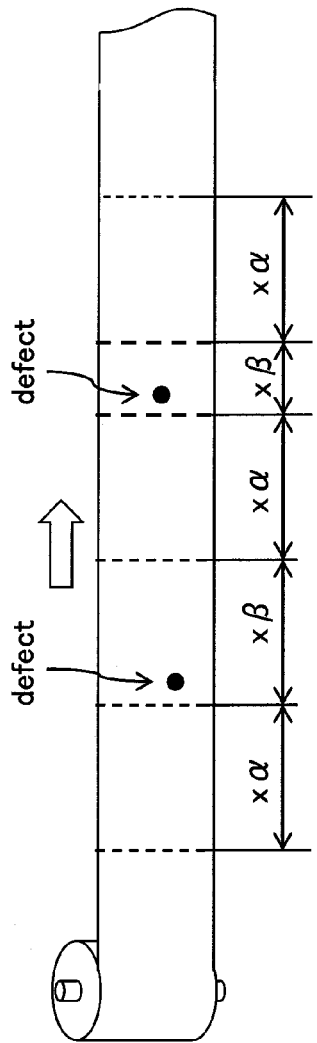
FIG. 16 illustrates a slitting position information generated as a result of calculation by the method shown in FIG. 13.
Figure 18:
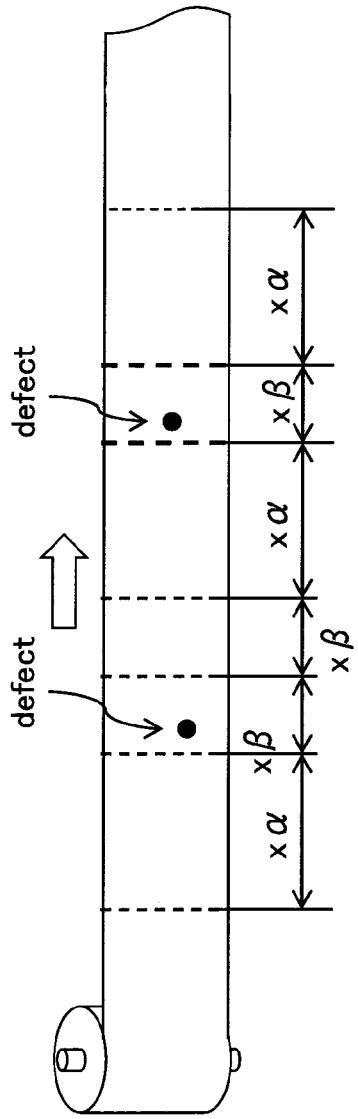
FIG. 18 illustrates a slitting position information generated as a result of calculation by the method shown in FIG. 15.

FIG. 12 is a schematic diagram illustrating a method for calculating slitting positions for defining defective regions and normal regions on a continuous inspected optical film laminate 10. FIG. 13 to FIG. 15 are flowcharts showing a method for calculating slitting positions on the continuous inspected optical film laminate. FIG. 16 to FIG. 18 illustrate how a slitting position information is determined as a result of calculation by the above different methods.

Calculation method of slitting position information is explained in the following with reference to FIG. 12 to FIG. 18. First, as described above, the continuous inspected optical film laminate 10 is fed out (step 1 in FIG. 13) and the identification means or indicia 20 provided on the optical film laminate is read by the mark reading unit 120 (step 2 in FIG. 13). In addition, a length measurement data is obtained from unrolled length of the continuous inspected optical film laminate 10. The information processing device 410 reads out the defect information 80 from the information storage medium 800 or the storage device 420 in response to the reading of the identification means 20.

In step 3 and step 4 in FIG. 13, the slitting position calculation means 415 compares a length of a sheet of the optical film laminate and the length xα corresponding to a normal region, based on the defect information 80 and the length measurement data. First, in step 3, the slitting position calculation means 415 calculates the distance or length x from a reference position (for example, the position A in FIG. 12, which is a first slitting position) to the position of the defect. In step 4, the slitting position calculation means 415 calculates a distance (x−xα)=x', where xα is the length of the normal region Xα. The length xα which is the length of the normal region Xα of the continuous inspected optical film laminate is determined by a system administrator based on the size of the liquid-crystal panel and pre-stored in the storage device 420. Then, the slitting position calculation means 415 determines whether the calculated length x' is larger or smaller than the length xα which is the length of the normal region Xα of the optical film laminate pre-stored in the storage device 420.

If a relation x'>xα is established, it is interpreted that a normal region Xα can be obtained from this part of the continuous inspected optical film laminate. Thus, the slitting position calculation means 415 determines that a position B on the upstream side of the continuous inspected optical film laminate spaced apart by the length xα from the position A (the first slitting position) to be a next slitting position (a second slitting position) (step 6). Similarly, the slitting position calculation means 415 calculates a length by subtracting the length xα which is the length of the normal region from the length of the second slitting position B. When the resulting length is larger than the length xα, a position C is determined on the upstream side of the optical film laminate spaced apart by the length xα from the position B (the second slitting position) as a third slitting position, then similarly a next position D is determined as a fourth slitting position, and so on.

To the contrary, if the relation x'≦xα is established, i.e., X''' in FIG. 12 ≦xα, a normal region Xαcannot be obtained from this part of the continuous inspected optical film laminate. In this case, the slitting position calculation means 415 adds a predetermined length x0 to x''' to calculate a length (x'''+x0)=xβ which is the length of the defective region Xβ. That is, a position E on the upstream side of the continuous inspected optical film laminate spaced apart by the length xβ is the slitting position to form a defective polarizing sheet Xβ corresponding to a defective region of the optical film laminate (step 6).

As described above, the slitting position calculation means 415 operates to perform calculations of the following (a) and (b) by using the defect information 80 read out from the information storage medium 800 or the storage device 420 in response to reading of the identification means 20 and a length measurement data calculated from the feed length of the optical film laminate, and calculates to determine these positions as next slitting positions:

(a) a distance xα to the next slitting position, if x'>xα; and
(b) a distance (x'+x0=xβ) to the next slitting position, if x'≦xα.

By the way, as a result of calculation of the slitting position calculation means 415, if the length (x'+x0=xβ) which is the length of the defective region Xβ becomes equal to the length xα which is the length of the normal region Xα, i.e., if (x'+x0)=(xα), the information processing device 410 cannot identify or discriminate the defect-free region Xα from the defective region Xβ. This means that the defective region Xβ may not be correctly recognized as the defective region, so that, for example, the information processing device 410 cannot discriminate the defect-free region Xα from the defective region Xβ. It is assumed that such situation occurs when the position of a defect in the optical film laminate is infinitely close to the next slitting position in the optical film laminate, or when a plurality of a series of defects are distributed over a length xα. Therefore, when (x'+x0)=xα, it is preferable to provide any of the following methods so that the information processing device 410 can identify or discriminate a normal region Xα and a defective region Xβ.

In the above (b), even if, as the result of calculation by the slitting position calculation means 415, the distance (x'+x0) to the next slitting position becomes equal to the length xα, that region may not be essentially the normal region xα. In order to make it possible to recognize such difference, in one embodiment of the present invention, as shown by step 5 in FIG. 13, data representing a normal region and a defective region is respectively associated with a slitting position information. For example, when a result of calculation by the slitting position calculation means 415 becomes (x'+x0)=xα, the information processing device 410 may associate a defective-region-representing value $X\gamma=1$ with either one of the slitting position or a slitting position preceding to the particular previous slitting position, as shown in FIG. 16. In other cases, when $x'>x\alpha$, the information processing device 410 may associate a normal-region-representing value $X\gamma=0$ with either one of the slitting position or a slitting position which precedes the particular previous slitting position. When $x\beta<x\alpha$, the defective-region-representing value $X\gamma=1$ is associated with the slitting position.

In another embodiment of the present invention, if, as the result of the calculation, the distance $(x'+x0)$ to the next slitting position becomes equal to the length $x\alpha$ which is the length of the normal region, the slitting position calculation means 415 corrects the calculation result so that the distance to the next slitting position satisfies the relation $(x'+x0')$, wherein $x0'>x0$, as shown in step 5 in FIG. 14. By calculating $x\beta=(x'+x0')$ different from $x\alpha$, this method makes it possible to allow for identifying or discriminating the region having the length $(x'+x0')$, i.e., the defective region $X\beta$ from the normal region $X\alpha$.

In yet another embodiment of the present invention, if, as the result of the calculation, the length $(x'+x0)$ to the next slitting position becomes equal to the length $x\alpha$, the slitting position calculation means 415 corrects the calculation result so that the length to the next slitting position becomes $[(x'+x0)/m]$ (wherein m=2 or more, preferably 2 or 3). As shown in FIG. 18, by calculating $x\beta=[(x'+x0)/m]$ different from $x\alpha$, this method makes it possible to allow for identifying or discriminating the region having the length $[(x'+x0)/m]$, i.e., the defective region $X\beta$, from the normal region $X\alpha$.

Summarizing the above, as a method for creating information for identifying or discriminating the normal region $X\alpha$ and defective region $X\beta$, either of the following methods may be adopted:

(1) A method of creating $X\gamma$ as information for identifying or discriminating the defective region $X\beta$ having a length $(x'+x0)$ from the normal region $X\alpha$;

(2) A method of creating a length to the next slitting position, as a length $(x'+x0')$ (wherein $x0'>x0$) which is different from the length $x\alpha$; and (3) A method of creating a length $[(x'+x0)/m]$ (wherein m=2 or more) to the next slitting position, which is different from the length $x\alpha$.

Particularly, in cases where the method (2) or (3) is carried out, $(x'+x0)=x\alpha$ is corrected to $(x'+x0')\neq x\alpha$ or $[(x'+x0)/m]\neq x\alpha$ after a correction by the slitting position calculation means 415. Thus, the next slitting position information can be used as information indicating the defective region $X\beta$ identified or discriminated over the normal region $X\alpha$ (i.e., information corresponding to $X\gamma$ in the method (1) above).

When the slitting position is determined, then in step 7, the information processing device 410, in case of the above (1), associates a length to the determined next slitting position with information $X\gamma$ and stores in the storage device 420. In case of (2) or (3) above, the information processing device 410 stores a length to next slitting position determined in step 6 to the storage device 420.

(Formation of Slit Line)

The optical film laminate is conveyed to the slitting station A after the identification means 20 thereon is read by the identification means reading unit 120. The slitting unit 150 sequentially forms slit lines on the optical film laminate based on the slitting position information determined by the slitting position calculation means 415 and the length measurement data of the optical film laminate (i.e., the slitting unit 150 half-cuts the optical film laminate). Any well-known cutting device such as, for example, a laser cutting device or other cutting device may be used as the slitting unit 150.

(Checkup of Slitting Position)

The slitting unit 150 sequentially forms slit lines on the optical film laminate in transverse direction with respect to the feed direction of the optical film laminate at the slitting station A based on the slitting position information. However, it is difficult to improve product accuracy of liquid-crystal display element unless the sequentially formed slit lines are precisely positioned. Therefore, it is important to precisely form slit lines on the optical film laminate in the continuous manufacturing system and method for liquid-crystal display elements.

Figure 19:
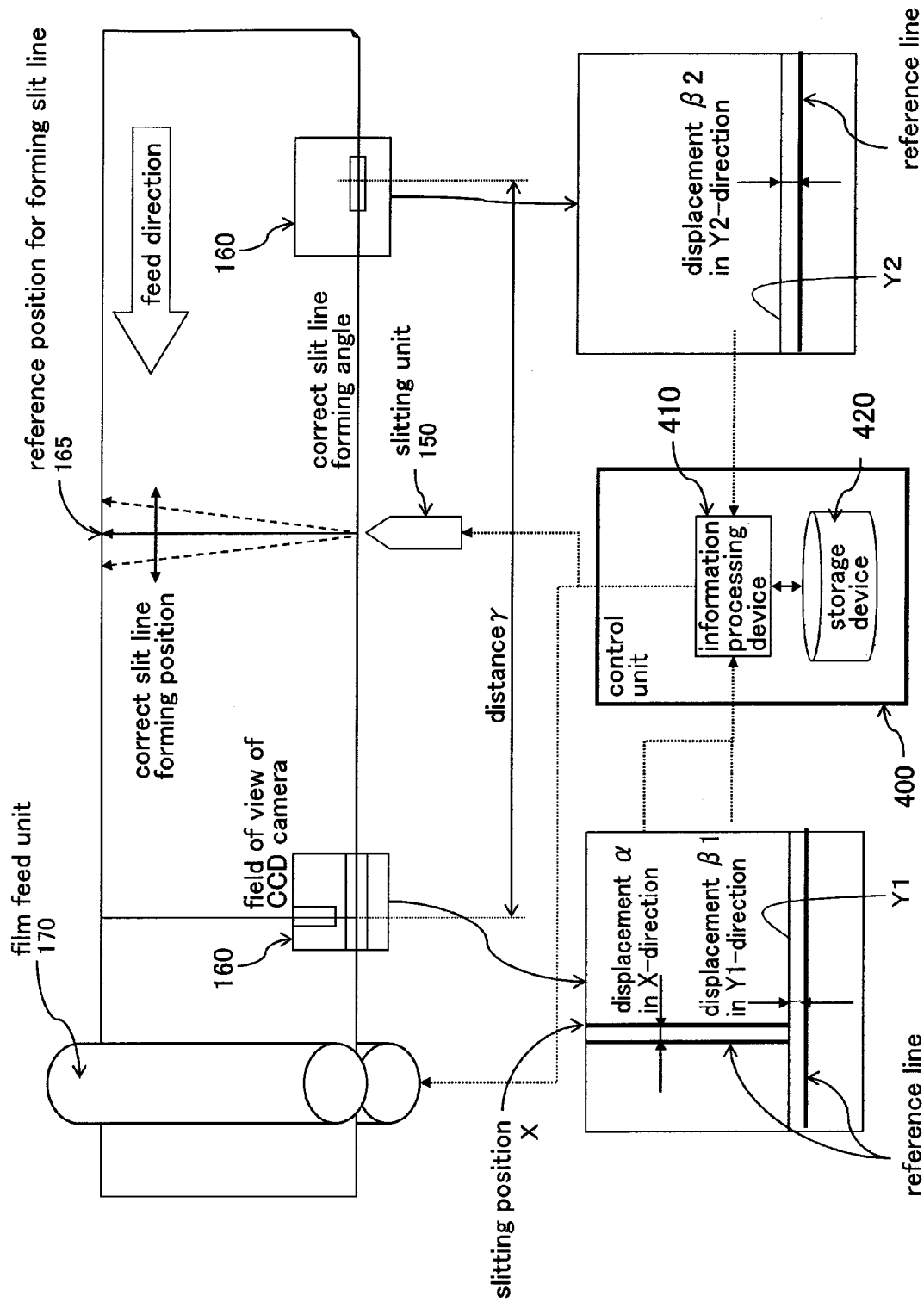
FIG. 19 illustrates an operation of a slitting position check-up unit in a continuous manufacturing system for liquid-crystal display element including an information storage-readout-calculation system according to one embodiment of the present invention.

FIG. 19 is a schematic diagram illustrating an operation of the slitting position check-up unit 160 (step 6 in FIG. 4). The slitting position checkup unit 160 checks a deviation between the positions of the actually formed slit line on the continuous inspected optical film laminate in a transverse direction with respect to a feed direction of the optical film laminate and the position calculated by the slitting position calculation means 415. Two slitting position checkup units 160 are provided, one on upstream of and one downstream of the slitting unit 150 as seen in the feed direction of the continuous inspected optical film laminate 10. A film feed unit 170 including a feed roller is disposed at the downstream side of the downstream slitting position checkup unit 160, whereby the feed of the continuous inspected optical film laminate 10 is re-started after a very short stop for forming a slit line. On the other hand, a speed adjustment unit 140 including a dancer roller is disposed at the upstream side of the upstream slitting position checkup unit 160, whereby the feed of the optical film laminate by the film feed unit 170 is maintained even if the feeding of the continuous inspected optical film laminate 10 is shortly stopped during the period of forming a slit line.

Coincidence of the position of the actually formed slit line in a transverse direction with respect to the feed direction of the continuous inspected optical film laminate 10 can be affirmed by determining the accurate positions in the traveling direction (X direction) and the transverse direction (Y direction) of the continuous inspected optical film laminate 10. One preferable way for checkup is to carry out at two locations, one on upstream side of and one on downstream side of the slitting position, for the deviation in X and Y directions between the actual slitting position and the edge (the side end) of the continuous inspected optical film laminate and respective reference lines at those positions. For example, the slitting position checkup unit 160 may be provided with a CCD camera to take images of the actual slitting position on the continuous inspected optical film laminate and the edge of the continuous inspected optical film laminate to produce picturized images. The respective reference lines corresponding to the actual slit lines and the edge of the continuous inspected optical film laminate are preliminarily provided in the image-taking regions. The reference line indicates slitting position calculated by the slitting position calculation means 415. The slitting position and the edge position of the continuous inspected optical film laminate 10 are determined in terms of differences in contrasts in the captured images. Then, a calculation is made to determine the distance (deviation) between the predetermined reference lines and the positions of the actual slit line and the edge of the continuous inspected optical film laminate, and the position and the angular position of the slitting unit 150 is corrected based on the calculated distance (deviation).

Specifically, the inspection for determining the deviation between the position of the actual slit line and the position calculated by the slitting position calculation means 415 is carried out for example in accordance with the following procedures.

(1) Images of the position (X) of the actual slit line and two positions (Y1, Y2) of the edge of the optical film laminate are taken by the slitting position checkup unit 160 including a CCD camera, and the position of the actual slit line (X) and the positions of the edges (Y1,Y2) are determined in terms of the differences in contrast.

(2) There is a slitting reference position 165 extending in Y direction at a position intermediate between a reference line extending in Y direction at an upstream position as seen in X direction in the imaging area of one of the slitting position checkup unit 160, and another reference line extending in Y direction at a downstream position as seen in X direction in the imaging area of the other of the slitting position checkup unit 160, and data γ representing the distance between the upstream and downstream reference lines is preliminarily stored in the storage device 420. Furthermore, there is a downstream reference line extending in the X direction in the image-taking region of the slitting position checkup unit 160.

(3) A correction value a for correcting the position of the slit line X and a correction value δ for angularly correcting the position of the slit line are calculated based on the measured positions of the actually formed slit line (X) and the edge (Y1, Y2) and the reference lines. The correction value α correspond to the measured deviation α, or the deviation α between the actual slit-line position (X) and the downstream side reference line extending in the Y direction. The correction value δ can be calculated according to the following equation, based on the deviations in Y direction of the edge of the continuous optical film laminate 15 at two positions, or the deviations (β1, β2) of the edge of the continuous optical film laminate with respect to respective ones of the upstream and downstream reference lines extending in the X direction, and the distance data γ between the two reference lines.

$$\delta = \cos^{-1}\left\{\frac{\gamma}{\sqrt{\gamma^2 + (\beta_1 - \beta_2)^2}}\right\}$$ [Equation 1]

(4) The storage device 420 is used to store correction values (α, δ) for applying an instruction to the slitting unit 150 to perform an angular position correction by a value δ and a positional correction by value α in the X direction based on the measured and calculated data so as to make the slit line conform to the reference line of the position where the slit line is to be formed extending in the Y direction.

(5) The slitting unit 150 corrects, when forming a next slit line, position in the feed direction and an angular position in a transverse direction with respect to the feed direction, based on the stored correction values (α, δ) so that the slit line conforms to the reference line.

(6) The slitting unit 150 operates to form a next slit line in the continuous inspected optical film laminate.

Figure 20:
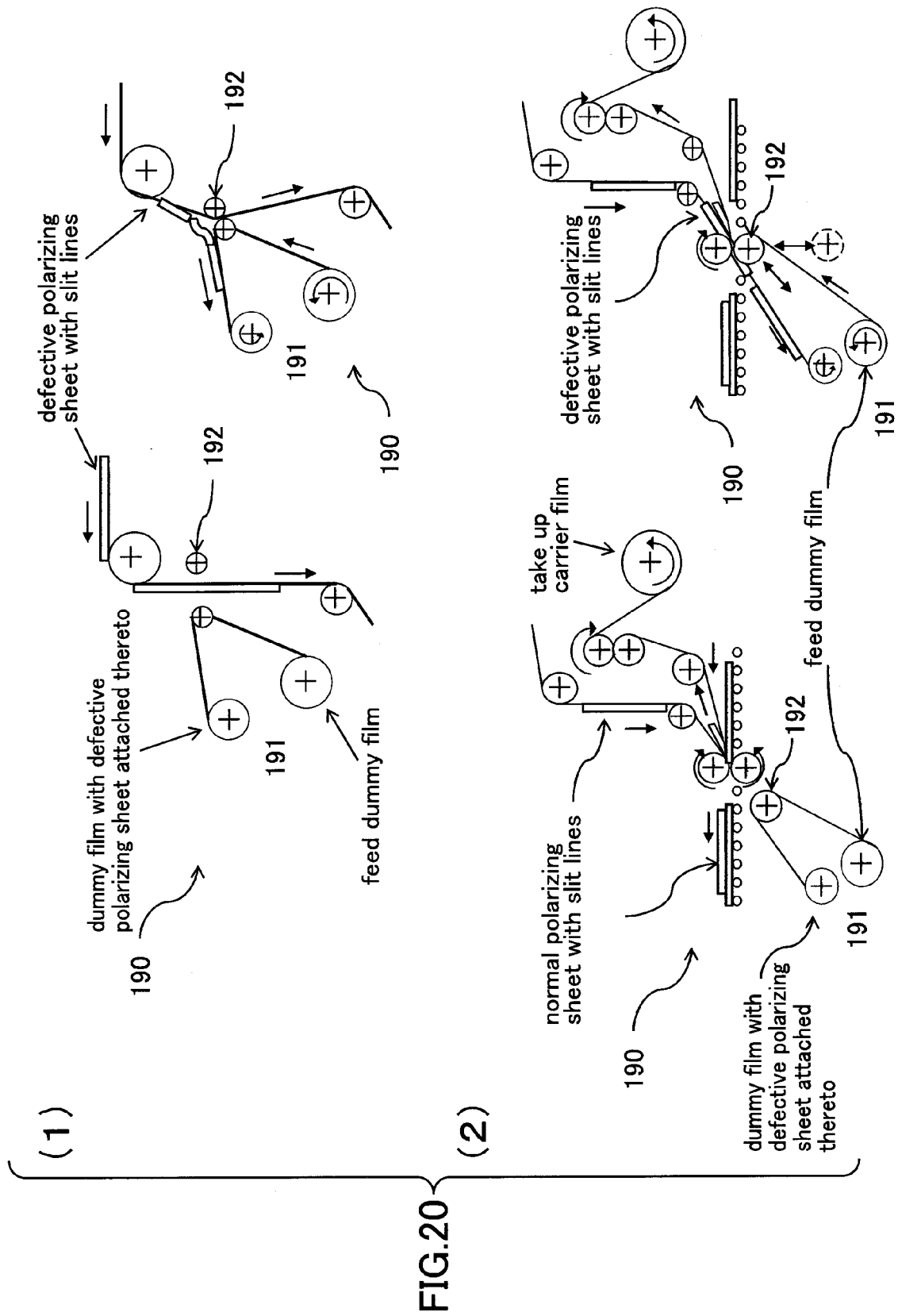
FIG. 20 illustrates a defective polarizing sheet removal unit which operates to identify or to select defective polarizing sheets, in a continuous manufacturing system for liquid-crystal display element including an information storage-readout-calculation system according to one embodiment of the present invention.

The continuous inspected optical film laminate 10 is conveyed to the removal station C after slit lines are formed by the slitting unit 150. Normal polarizing sheets Xα and defective polarizing sheets Xβ of the polarizing composite film 11 are releasably held in cut-state by respective slit lines on the carrier film 14 of the continuous inspected optical film laminate 10 conveyed to the removal station C. A defective polarizing sheet removal unit 190 of the removal station C operates to identify or discriminate the defective polarizing sheets Xβ included in the continuous inspected optical film laminate, and peels and removes them from the carrier film 14 (step 9 in FIG. 4). FIG. 20(1) and FIG. 20(2) show the defective polarizing sheet removal unit 190 which operates to identify or discriminate a defective polarizing sheet Xβ. The defective polarizing sheet removal unit 190 identifies or discriminates only the defective polarizing sheets Xβ over the normal polarizing sheets based on identification information Xγ of defective polarizing sheet as shown in FIG. 13 and FIG. 16, or, may identify or discriminate the defective polarizing sheets Xβ based on lengths of the normal polarizing sheet Xα and the defective polarizing sheets Xβ as shown in FIG. 14, FIG. 15, FIG. 17, and FIG. 18.

The defective polarizing sheet removal unit 190 in FIG. 20 (1) comprises a dummy film drive mechanism 191 for feeding a dummy film so that the defective polarizing sheet Xβ releasably laminated to the continuous carrier film 14 is peeled and attached to the dummy film, and a moving unit 192 adapted to be activated when the defective polarizing sheet Xβ reaches a removal initiation point for the defective polarizing sheet in a feed path of the optical film laminate. The moving unit 192 is a unit adapted to shift the continuous inspected optical film laminate 10 for peeling and attaching the laminate to the dummy film in the dummy film feed path of the dummy film drive mechanism 191.

The defective polarizing sheet removal unit 190 in FIG. 20 (2) is configured to be operated in an inter-related manner with the lamination unit 200 including a pair of lamination rollers provided at the lamination station B. The unit 190 comprises a dummy film drive mechanism 191 for feeding a dummy film so that the defective polarizing sheet Xβ releasably laminated on the continuous carrier film 14 is peeled and attached to the dummy film, and a movable roller 192 defining a dummy film feed path of the dummy film drive mechanism 191. The removal unit in FIG. 20 (2) is different from the removal unit in FIG. 20 (1) in that, in the removal unit in FIG. 20 (2), the movable roller 192 defining the dummy film feed path disposed adjacent to the pair of lamination rollers of the lamination unit 200 at the lamination station B is arranged in a inter-related manner with the lamination rollers in the lamination unit 200. More specifically, when the defective polarizing sheet Xβ reaches an end position (i.e., the removal initiation point) of the feed path of the optical film laminate, the control unit 400 instructs the pair of lamination rollers to shift apart from each other and the movable roller 192 defining the dummy film feed path to shift to a nip between the lamination rollers which are in spaced-apart relation to replace the roller with one of the rollers of the pair of the lamination rollers, to operate the movable roller 192 and the other laminating roller in an inter-related manner. In this instance, the carrier film 14 is taken up by the carrier film take up drive mechanism 210, and the defective polarizing sheet Xβ is peeled from the carrier film 14 and the peeled defective polarizing sheet Xβ is attached to the dummy film in the dummy film feed path by means of the movable roller 192 operated in an inter-related manner with the other roller of the pair of the lamination roller, and is removed.

(Conveyance of Liquid-Crystal Panel and Lamination with Normal Polarizing Sheet)

Figure 21:
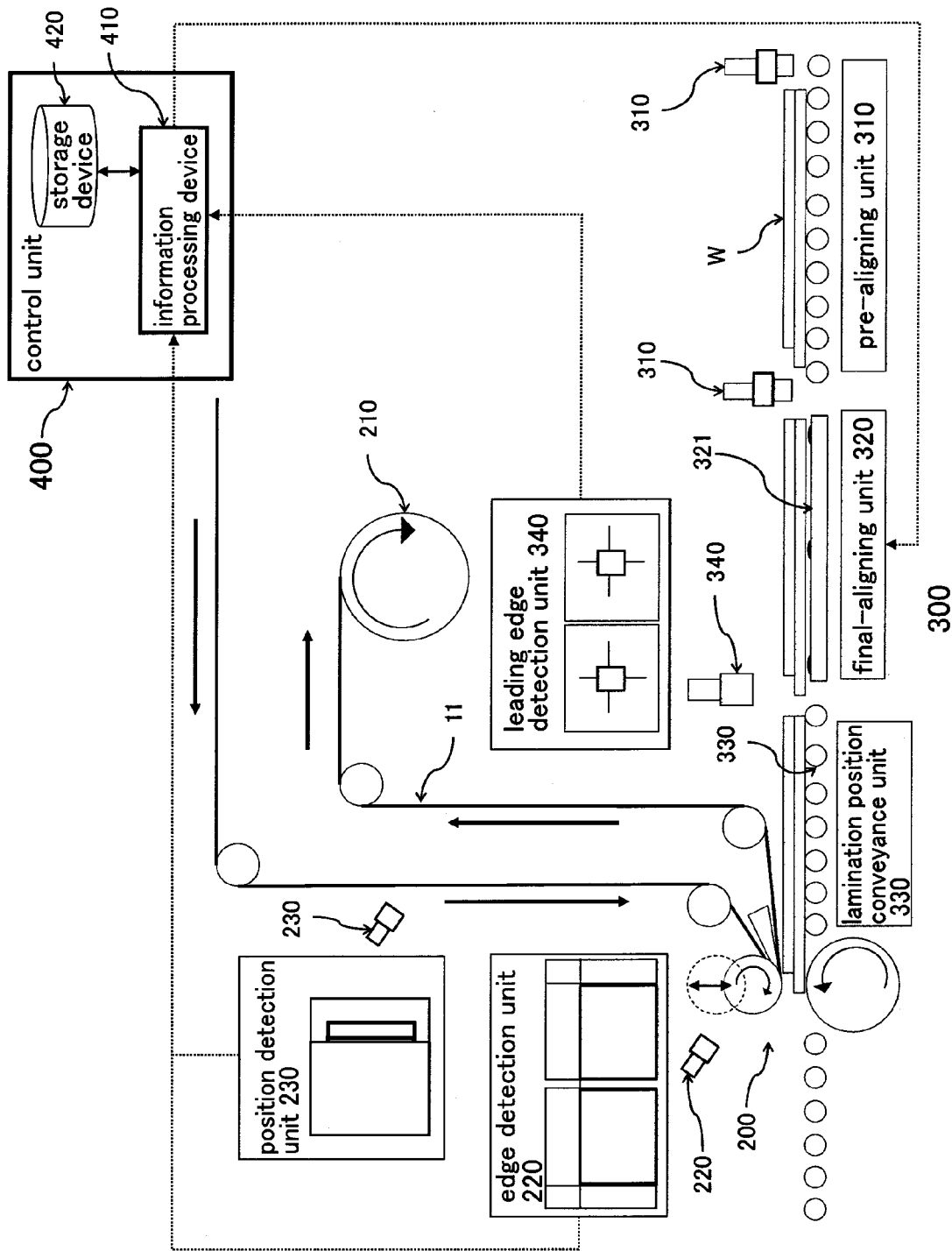
FIG. 21 illustrates posture-controlled liquid crystal panels being conveyed to a lamination position, in a continuous manufacturing system for liquid-crystal display element including an information storage-readout-calculation system according to one embodiment of the present invention.
Figure 22:
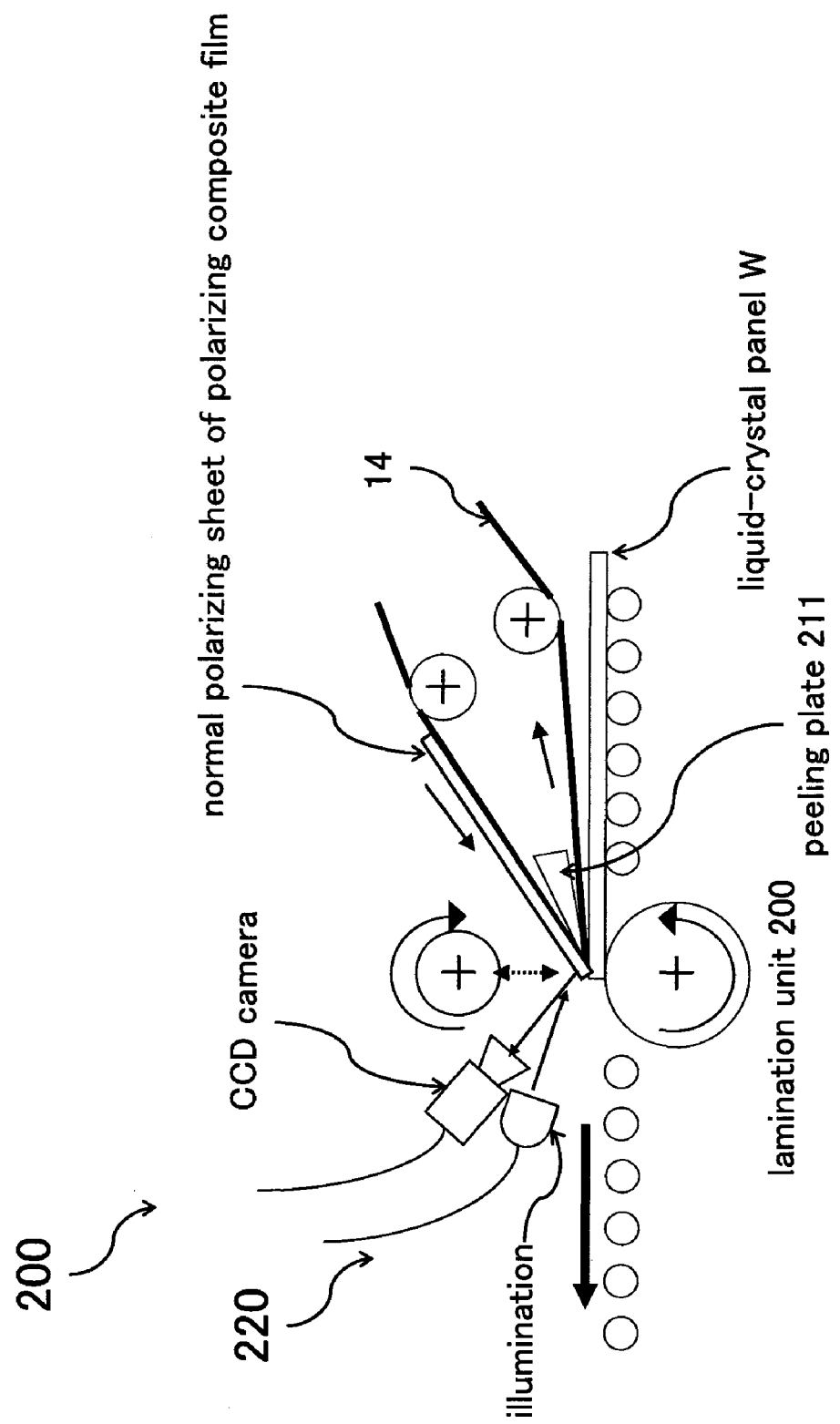
FIG. 22 illustrates a lamination unit for laminating normal polarizing sheets and liquid-crystal panels, in a continuous manufacturing system for liquid-crystal display element including an information storage-readout-calculation system according to one embodiment of the present invention.

The continuous inspected optical film laminate 10, having defective polarizing sheets Xβ removed at the removal station C and only normal polarizing sheets Xα existing on the continuous carrier film 14, is then conveyed to the lamination station B. In another embodiment adopting the removal unit shown in FIG. 20 (2), the continuous inspected optical film laminate having normal polarizing sheets Xα and defective polarizing sheets Xβ formed on the continuous carrier film 14 is conveyed to the lamination station B. Although lamination of liquid-crystal panel and normal polarizing sheets Xα is described herein with respect to the former embodiment, the latter embodiment is the same as the former embodiment, except that defective polarizing sheets Xβ are removed at the lamination station B. FIG. 21 is a schematic diagram showing the manner of conveying liquid-crystal panel to a lamination position in a posture-controlled state by controlling a pre-alignment unit 310, a final-alignment unit 320, a conveyance unit 330 for conveying the panels to the lamination position, and a panel-edge detection unit 340 in the liquid-crystal panel conveyance unit. FIG. 22 illustrates a lamination unit for laminating a normal polarizing sheet to a respective one of liquid-crystal panel W, comprising an edge detection unit 220 for detecting the leading edge of normal polarizing sheet Xα and a peeling plate 211 for bending the continuous carrier film 14 in an acute angle to peel a normal polarizing sheet Xα.

The liquid-crystal panels W are taken out one-by-one from a magazine containing a large number of liquid-crystal panels, by means of a liquid-crystal-panel supply unit, and conveyed through cleaning/polishing stage to the lamination unit 200 at the lamination station by a liquid-crystal panel conveyance unit 300, by being adjusted to equal intervals and a constant transportation speed. The liquid-crystal panel conveyance unit 300 comprises a liquid-crystal posture control device including, as shown in FIG. 21, a pre-alignment unit 310, a final-alignment unit 320, a conveyance unit 330 for conveying the panels to the lamination position, and a panel-edge detection unit 340. The conveyance unit 300 aligns the orientation of the liquid-crystal panel W, when the normal polarizing sheet Xα is transported to the lamination station B, in synchronization with the transportation of the normal polarizing sheet Xα.

Supplying speed of normal polarizing sheets Xα on the continuous carrier film 14 to the lamination unit 200 at the lamination station B is preferably adjusted to a constant speed. As shown in FIG. 21 or FIG. 22, the continuous carrier film 14 is bent in an acute angle by the peeling plate 211 at the lamination station B to peel the normal polarizing sheet Xα. Bending the continuous carrier film 14 in an acute angle allows gradually exposing an adhesive layer of the normal polarizing sheet Xα. As a result, the leading edge of the normal polarizing sheet Xα is slightly exposed to facilitate an alignment with the leading edge of a liquid-crystal panel W.

The leading edge of the normal polarizing sheet Xα is shifted to the nip defined between the pair of lamination rollers of the lamination unit 200 when the rollers are in the vertically spaced apart relation to each other. Although the normal polarizing sheet Xα is fed in a state laminated on the continuous carrier film 14, it is seldom that the normal polarizing sheet Xα is accurately fed so that the angle θ between its feed direction and the lengthwise direction of the continuous carrier film 14 becomes zero. Therefore, deviations of the normal polarizing sheet Xα in the feed direction and the transverse direction are measured, for example, by taking images of the sheet using the CCD camera of the straight-ahead-posture or position detection unit 230 and subjecting the taken images to an image processing, whereby the measured deviations are calculated in terms of a distance in lengthwise direction x, a distance in a direction perpendicular to the lengthwise direction y and an angle between the feed direction and the lengthwise direction θ (step 10 in FIG. 4).

On the other hand, liquid-crystal panels W are sequentially supplied one-by-one at a constant interval and speed from a supplying unit, and the posture of the panels are controlled by a liquid-crystal panel conveyance unit 300 as shown in FIG. 21. The posture control is now explained with reference to FIG. 21.

Figure 1:
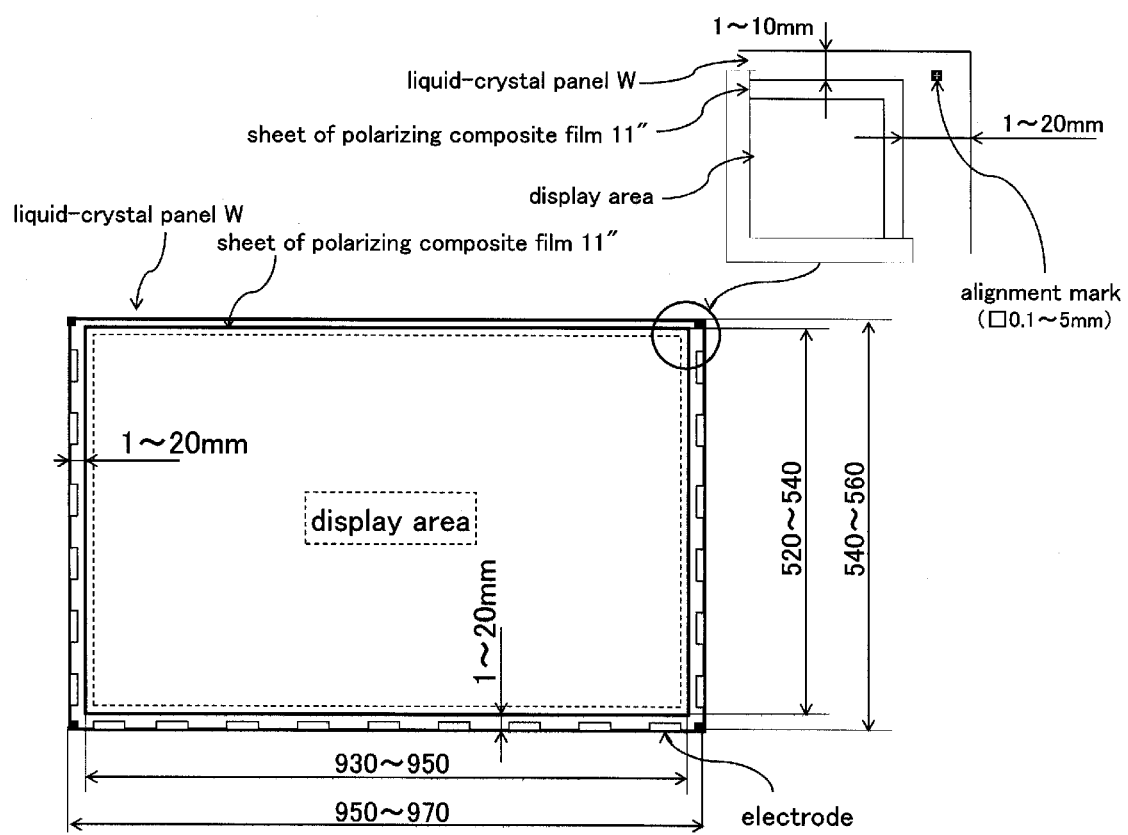
FIG. 1 illustrates a typical example of a liquid-crystal display element for a widescreen television having a diagonal screen size of 42 inches.

The liquid-crystal panels W are roughly positioned by the pre-alignment unit 310, so that they are aligned in lengthwise direction and a direction perpendicular to the lengthwise direction respectively with the feed direction and the direction transverse to the feed direction in the conveyance path (step 12 in FIG. 4). The positioned liquid-crystal panel W is conveyed to and placed on the final-alignment unit 320 which includes a turnable alignment table 321. The leading edge of the liquid-crystal panel W placed on the alignment table 321 is detected by the panel-edge detection unit 340 (step 13 in FIG. 4). The position of the detected leading edge of the liquid-crystal panel W is checked for match with the reference lamination position stored in the storage device 420, specifically, the calculation data in terms of x, y and θ to represent the orientation of the normal polarizing sheet Xα to be laminated to the liquid-crystal panel W. For example, the deviation between the leading edge of the liquid-crystal panel W and the reference lamination position is measured using an alignment mark of the liquid-crystal panel W illustrated in FIG. 1 to calculate the angular displacement θ, and the alignment table 321 having the liquid-crystal panel W placed thereon is turned by the angular displacement θ (step 14 in FIG. 4). Then, the alignment table 321 is connected to the conveyance unit 330 directed for the lamination unit 200 at the lamination station B. The liquid-crystal panel W is conveyed to the lamination unit 200 by the conveyance unit 330, while keeping the same orientation (step 15 in FIG. 4). The leading edge of the liquid-crystal panel W is registered with and laid on the leading edge of the normal polarizing sheet Xα. In the final stage, the normal polarizing sheet Xα and the liquid-crystal panel W which are in aligned relation with each other and are held between the pair of lamination rollers and pressed thereby to obtain a finished liquid-crystal display element (step 16 in FIG. 4).

In the method and the system according the present invention, the normal polarizing sheet Xα is fed to the lamination unit 200 for lamination with the liquid-crystal panel W together with the carrier film 14 within the continuous inspected optical film laminate advanced under tension, so that there is least possibility that the periphery of the normal polarizing sheet Xα is bent or sagged and that the periphery of the normal polarizing sheet Xα is bowed or warped. This makes it easy to have the orientation of the liquid-crystal panel W aligned with the normal polarizing sheet Xα and makes the manufacturing speed of the liquid-crystal display element increased and the product accuracy improved. Such method and system have been unachievable in the manufacturing process utilizing the individualized sheets, the process utilizing the individualized sheets to complete a liquid-crystal display element includes steps of; after peeling a separator from each of the individualized sheets to expose the adhesive layer and feeding under a vacuum suction each of the sheets to a lamination position, adjusting the position of the sheet with respect to the liquid-crystal panel W and laminating the sheet to the liquid-crystal panel W.

Although the present invention has been described in connection with preferred embodiments, it will be understood that various changes and modifications will be made by those skilled in the art without departing from the spirit and scope of the invention, defined in the following claims, and legal equivalents of the following claims may be substituted for elements thereof. Accordingly, the present invention is not limited to the specific embodiments disclosed as the best mode for carrying out the invention, but intended to cover all embodiments included within the scope thereof.

The invention claimed is:

1. An information storage-readout-calculation system adapted for use in a manufacturing system for continuously manufacturing liquid-crystal display element by laminating sheets of polarizing composite film on a continuous optical film laminate to respective ones of a plurality of liquid-crystal panels, the continuous optical film laminate comprising a continuous polarizing composite film having an adhesive layer thereon and a continuous carrier film releasably laminated to the adhesive layer, the continuous optical film laminate having a width corresponding to either of a long or short side of the liquid-crystal panel, the system comprising;

a removable information storage medium storing information of position of at least one defect detected through a preliminary inspection of the continuous polarizing composite film included in the continuous optical film laminate, a roll of a continuous inspected optical film laminate provided with at least one identification means for identifying the continuous inspected optical film laminate, and a slitting position calculation means for determining defective-polarizing-sheet slitting positions and normal-polarizing-sheet slitting positions by using the position information read out from the removable information storage medium based on the at least one identification means and length measurement data calculated based on a feed length of the continuous inspected optical film laminate fed out from the roll, the defective-polarizing-sheet slitting positions and the normal-polarizing-sheet slitting positions defining positions of at least one defect-containing polarizing sheet having at least one defect and defect free polarizing sheets having no defect, respectively, whereby, the defective-polarizing-sheet slitting positions and the normal-polarizing-sheet slitting positions are usable in the manufacturing system of liquid-crystal display elements for respectively defining at least one defective-polarizing sheet and defect-free polarizing sheets by forming slit lines in the continuous inspected optical film laminate in a transverse direction with respect to the feed direction of the continuous inspected optical film laminate at a side opposite to the continuous carrier film to a depth reaching a surface of the carrier film adjacent to the adhesive layer.

2. The information storage-readout-calculation system as defined in claim 1, wherein the continuous inspected optical film laminate further comprises a continuous surface-protection film releasably laminated to a surface opposite to the adhesive layer of the continuous polarizing composite film.

3. A method for producing an information storage-readout-calculation system adapted for use in a manufacturing system for continuously manufacturing liquid-crystal display elements by laminating sheets of polarizing composite film on a continuous optical film laminate to respective ones of a plurality of liquid-crystal panels, the continuous optical film laminate comprising a continuous polarizing composite film having an adhesive layer thereon and a continuous carrier film releasably laminated to the adhesive layer, the continuous optical film laminate having a width corresponding to either of a long or short side of the liquid-crystal panel, the method comprising steps of;

manufacturing a roll of a continuous inspected optical film laminate provided with at least one identification means, by manufacturing a continuous polarizing composite film including a continuous polarizer and a continuous protective film laminated on at least one surface of the continuous polarizer, detecting at least one defect in the continuous polarizing composite film through a preliminary inspection of the continuous polarizing composite film, manufacturing the continuous inspected optical film laminate by releasably laminating a continuous carrier film to the adhesive layer of the continuous polarizing composite film, generating at least one identification means for identifying the continuous inspected optical film laminate and applying the at least one identification means to the continuous inspected optical film laminate, and winding the continuous inspected optical film laminate provided with the at least one identification means to form the roll of the continuous inspected optical film laminate;

storing information relating to position of the at least one defect detected through the preliminary inspection into a removable prepared storage medium to form a removable information storage medium having the position information stored therein; and providing a slitting position calculation means configured to determine defective-polarizing-sheet slitting positions and normal-polarizing-sheet slitting positions by using the position information read out from the removable information storage medium based on the at least one identification means and length measurement data calculated based on the feed length of the continuous inspected optical film laminate fed out from the roll, the defective-polarizing-sheet slitting positions and the normal-polarizing-sheet slitting positions defining at least one defect-containing polarizing sheet having at least one defect and defect free polarizing sheets having no defect, respectively.

4. The method as defined in claim 3, wherein the step of manufacturing a roll of a continuous inspected optical film laminate further comprises a step of releasably laminating a continuous surface-protection film to a surface opposite to the adhesive layer of the continuous polarizing composite film.

5. The method as defined in claim 3, wherein the step of manufacturing a roll of a continuous inspected optical film laminate further comprises at least one of the steps of:

inspecting a surface of the continuous polarizing composite film by means of reflected light, inspecting inside of the continuous polarizing composite film by transmitting light irradiated from a light source through the continuous polarizing composite film to detect any defect existing in the continuous polarizing composite film as one or more shades, or, detecting any defect as one or more bright spots by cross-Nichol transmission inspection designed such that the light irradiated from a light source is projected to the continuous polarizing composite film and a polarization filter, and the light which has transmitted through the continuous polarizing composite film and the polarization filter is examined, with absorption axes of the continuous polarizing composite film and polarization filter being oriented at a right angle.

6. A method for producing an information storage-readout-calculation system adapted for use in a manufacturing system for continuously manufacturing liquid-crystal display elements by laminating sheets of polarizing composite film provided on a continuous optical film laminate to respective ones of a plurality of liquid-crystal panels, the continuous optical film laminate comprising a continuous polarizing composite film having an adhesive layer thereon and a continuous carrier film releasably laminated to the adhesive layer, the continuous optical film laminate having a width corresponding to either of a long or short side of the liquid-crystal panel, the method comprising steps of:

- manufacturing a roll of a continuous inspected optical film laminate provided with at least one identification means, by preparing a roll of continuous provisional optical film laminate including a continuous polarizing composite film having an adhesive layer thereon and a continuous provisional carrier film releasably laminated to the adhesive layer, exposing the continuous polarizing composite film having an adhesive layer thereon by peeling the continuous provisional carrier film from the continuous provisional optical film laminate while feeding the continuous provisional optical film laminate from the roll, detecting at least one defect in the continuous polarizing composite film having the adhesive layer thereon through a preliminary inspection of the exposed continuous polarizing composite film having an adhesive layer thereon, manufacturing the continuous inspected optical film laminate by releasably laminating a continuous carrier film to the adhesive layer of the continuous polarizing composite film, generating at least one identification means for identifying the continuous inspected optical film laminate and applying the identification means to the continuous inspected optical film laminate, and winding the continuous inspected optical film laminate provided with the at least one identification means to form the roll of the continuous inspected optical film laminate;
- storing information of position of the at least one defect detected through the preliminary inspection in a prepared removable storage medium to form a removable information storage medium having the position information stored therein; and,
- providing slitting position calculation means configured to determine defective-polarizing-sheet slitting positions and normal-polarizing-sheet slitting positions by using the position information read out from the removable information storage medium based on the at least one identification means and length measurement data calculated based on a feed length of the continuous inspected optical film laminate fed out from the roll, the defective-polarizing-sheet slitting positions and the normal-polarizing-sheet slitting positions defining at least one defect-containing polarizing sheet having at least one defect and defect-free polarizing sheets having no defect, respectively.

7. The method as defined in claim 6, wherein the continuous provisional carrier film has a transferable adhesive layer formed by subjecting one of the opposite surfaces of the film to a releasing treatment, applying a solvent containing adhesive to the treated surface, and then drying the film the solvent is applied.

8. The method as defined in claim 6, wherein the continuous carrier film has been subjected to a releasing treatment at the surface which is to be laminated to the exposed adhesive layer of the continuous polarizing composite film.

9. The method as defined in claim 6, wherein the step of manufacturing a roll of a continuous inspected optical film laminate further comprises a step of releasably laminating a continuous surface-protection film to a surface opposite to the adhesive layer of the continuous polarizing composite film.

10. The method as defined in claim 6, wherein the step of manufacturing a roll of a continuous inspected optical film laminate further comprises at least one of the steps of:

- inspecting a surface of the continuous polarizing composite film by means of reflected light,
- inspecting inside of the continuous polarizing composite film by transmitting light irradiated from a light source through the continuous polarizing composite film to detect any defect existing in the continuous polarizing composite film as one or more shades, and,
- detecting any defect as one or more bright spots by cross-Nichol transmission inspection designed such that the light irradiated from a light source is projected to the continuous polarizing composite film and a polarization filter, and the light which has transmitted through the continuous polarizing composite film and the polarization filter is examined, with absorption axes of the continuous polarizing composite film and polarization filter being oriented at a right angle.

* * * * *